United States Patent
Voris et al.

(10) Patent No.: US 7,335,374 B2
(45) Date of Patent: Feb. 26, 2008

(54) MULTI-LAYER BARRIER PREVENTING WOOD PEST ACCESS TO WOODEN STRUCTURES

(75) Inventors: Peter Van Voris, Richland, WA (US); Dominic A. Cataldo, Kennewick, WA (US); Frederick G. Burton, Stansbury Park, UT (US)

(73) Assignee: Battelle Memorial Institute K1-53, Richland, WA (US)

( * ) Notice: Subject to any disclaimer, the term of this patent is extended or adjusted under 35 U.S.C. 154(b) by 191 days.

(21) Appl. No.: 10/889,706

(22) Filed: Jul. 13, 2004

(65) Prior Publication Data
US 2004/0247637 A1 Dec. 9, 2004

Related U.S. Application Data

(60) Division of application No. 09/353,494, filed on Jul. 13, 1999, now Pat. No. 6,803,051, which is a continuation of application No. 09/030,690, filed on Feb. 25, 1998, now Pat. No. 5,985,304.

(51) Int. Cl.
*A01N 25/10* (2006.01)
(52) U.S. Cl. .................. 424/411; 424/405; 424/406; 424/409; 514/531; 523/122
(58) Field of Classification Search .......... 424/405, 424/409, 411; 523/122; 514/531
See application file for complete search history.

(56) References Cited

U.S. PATENT DOCUMENTS

| | | |
|---|---|---|
| 1,999,458 A | 4/1935 | Hollister |
| 2,269,626 A | 1/1942 | Henry |
| 2,899,771 A * | 8/1959 | Burris, Jr. ............ 52/169.14 |
| 2,970,404 A | 2/1961 | Beaufils et al. |
| 3,111,403 A | 11/1963 | Soper |
| 3,231,398 A | 1/1966 | Pauli |
| 3,235,366 A | 2/1966 | Seymour et al. |
| 3,257,190 A | 6/1966 | Soper |
| 3,367,065 A | 2/1968 | Cravens |
| 3,384,993 A | 5/1968 | Kane |
| 3,502,458 A | 3/1970 | Schenk |
| 3,551,192 A | 12/1970 | Reinert |
| 3,592,792 A | 7/1971 | Newland et al. |
| 3,608,062 A | 9/1971 | Alfes et al. |
| 3,639,583 A | 2/1972 | Cardarelli et al. |
| 3,655,129 A | 4/1972 | Seiner |

(Continued)

FOREIGN PATENT DOCUMENTS

AU    16980/83 A    7/1983

(Continued)

OTHER PUBLICATIONS

Pesticide Manual, 175,178,196,659—1994.*

(Continued)

*Primary Examiner*—Neil S. Levy
(74) *Attorney, Agent, or Firm*—Nixon Peabody LLP

(57) ABSTRACT

A method and device are disclosed which prevent the intrusion of insects onto wood structures by using a barrier capable of retaining pesticide. In the disclosed method, the barrier maintains a minimal effective level of insecticide for a predetermined period of time.

56 Claims, 8 Drawing Sheets

U.S. PATENT DOCUMENTS

| | | | |
|---|---|---|---|
| 3,671,548 A | 6/1972 | Itaya et al. |
| 3,691,683 A | 9/1972 | Sterzik |
| 3,697,253 A | 10/1972 | MacMurray |
| 3,705,938 A | 12/1972 | Hyman et al. |
| 3,706,161 A | 12/1972 | Jenson |
| 3,716,560 A | 2/1973 | Taya et al. |
| 3,740,419 A | 6/1973 | Campbell |
| 3,741,807 A | 6/1973 | Horne |
| 3,759,941 A | 9/1973 | Sampei et al. |
| 3,835,176 A | 9/1974 | Matsuo et al. |
| 3,835,220 A | 9/1974 | Matsui et al. |
| 3,846,500 A | 11/1974 | Kitamura et al. |
| 3,851,053 A | 11/1974 | Cardarelli |
| 3,857,934 A | 12/1974 | Bernstein et al. |
| 3,864,114 A | 2/1975 | Green |
| 3,864,388 A | 2/1975 | Kitamura et al. |
| 3,867,542 A | 2/1975 | Ueda et al. |
| 3,876,681 A | 4/1975 | Okuno et al. |
| 3,880,643 A | 4/1975 | Cooke et al. |
| 3,891,423 A | 6/1975 | Stanley et al. |
| 3,899,586 A | 8/1975 | Okuno et al. |
| 3,906,089 A | 9/1975 | Okuno et al. |
| 3,939,606 A | 2/1976 | Vandemark et al. |
| 3,954,814 A | 5/1976 | Mizutani et al. |
| 3,966,963 A | 6/1976 | Okuno et al. |
| 3,970,703 A | 7/1976 | Kitamura et al. |
| 3,981,903 A | 9/1976 | Hirano et al. |
| 3,998,868 A | 12/1976 | Mizutani et al. |
| 4,003,945 A | 1/1977 | Kitamura et al. |
| 4,007,258 A | 2/1977 | Cohen et al. |
| 4,021,122 A | 5/1977 | Krenmayr |
| 4,037,352 A | 7/1977 | Hennart et al. |
| 4,063,919 A | 12/1977 | Grano, Jr. |
| 4,065,555 A | 12/1977 | Potter |
| 4,066,441 A | 1/1978 | Lutz et al. |
| 4,077,795 A | 3/1978 | Cooke et al. |
| 4,082,533 A | 4/1978 | Wittenbrook et al. |
| 4,101,582 A | 7/1978 | Lutz et al. |
| 4,102,991 A | 7/1978 | Kydonieus |
| 4,104,374 A | 8/1978 | Reuther et al. |
| 4,118,505 A | 10/1978 | Kitamura et al. |
| 4,123,250 A | 10/1978 | Kupelian |
| 4,160,335 A | 7/1979 | Von Kohorn et al. |
| 4,172,904 A | 10/1979 | Young et al. |
| 4,176,189 A | 11/1979 | Itaya et al. |
| 4,190,680 A | 2/1980 | Young et al. |
| 4,193,984 A | 3/1980 | Kydonieus |
| 4,198,441 A | 4/1980 | Young et al. |
| 4,198,782 A | 4/1980 | Kydonieus et al. |
| 4,200,664 A | 4/1980 | Young et al. |
| 4,205,096 A | 5/1980 | Young et al. |
| 4,212,879 A | 7/1980 | Ohsumi et al. |
| 4,212,897 A | 7/1980 | Young et al. |
| 4,229,469 A | 10/1980 | Mizutani et al. |
| 4,235,872 A | 11/1980 | Tocker |
| 4,237,113 A | 12/1980 | Cardarelli |
| 4,237,114 A | 12/1980 | Cardarelli |
| 4,243,703 A | 1/1981 | Palvarini et al. |
| 4,260,626 A | 4/1981 | Carr et al. |
| 4,263,463 A | 4/1981 | Kitamura et al. |
| 4,269,626 A | 5/1981 | Gorke et al. |
| 4,272,520 A | 6/1981 | Kydonieus et al. |
| 4,279,924 A | 7/1981 | Suzuki et al. |
| 4,282,207 A | 8/1981 | Young et al. |
| 4,282,209 A | 8/1981 | Tocker |
| 4,293,504 A | 10/1981 | Suzuki et al. |
| 4,320,113 A | 3/1982 | Kydonieus |
| 4,327,109 A | 4/1982 | Mizutani et al. |
| 4,336,194 A | 6/1982 | Ohsumi et al. |
| 4,344,250 A | 8/1982 | Fahlstrom |
| 4,348,218 A | 9/1982 | Bond, Jr. |
| 4,350,678 A | 9/1982 | Palvarini et al. |
| 4,352,833 A | 10/1982 | Young et al. |
| 4,360,376 A | 11/1982 | Koestler |
| 4,374,126 A | 2/1983 | Cardarelli et al. |
| 4,376,785 A | 3/1983 | Matsuo et al. |
| 4,377,675 A | 3/1983 | Daudt et al. |
| 4,400,374 A | 8/1983 | Cardarelli |
| 4,405,360 A | 9/1983 | Cardarelli |
| 4,435,383 A | 3/1984 | Wysong |
| 4,457,929 A | 7/1984 | Kamachi et al. |
| 4,496,586 A | 1/1985 | Matsui et al. |
| 4,500,337 A | 2/1985 | Young et al. |
| 4,500,338 A | 2/1985 | Young et al. |
| 4,500,339 A | 2/1985 | Young et al. |
| 4,503,071 A | 3/1985 | Hirano et al. |
| 4,508,568 A | 4/1985 | Fox |
| 4,576,801 A | 3/1986 | Parry et al. |
| 4,579,085 A | 4/1986 | McGuire |
| 4,639,393 A * | 1/1987 | Von Kohorn et al. .... 428/304.4 |
| RE32,356 E | 2/1987 | Cardarelli |
| 4,666,706 A | 5/1987 | Farquharson et al. |
| 4,666,767 A | 5/1987 | Von Kohorn et al. |
| 4,680,328 A | 7/1987 | Dohrer et al. |
| 4,747,902 A | 5/1988 | Saitoh |
| 4,767,812 A | 8/1988 | Chapin et al. |
| 4,808,454 A | 2/1989 | Saitoh |
| 4,818,525 A | 4/1989 | Kamada et al. |
| 4,842,860 A | 6/1989 | Sugiura et al. |
| 4,886,656 A | 12/1989 | Obayashi et al. |
| 4,921,703 A | 5/1990 | Higuchi et al. |
| 4,929,497 A | 5/1990 | Mitchell et al. |
| 4,971,796 A | 11/1990 | Sjogren |
| 5,019,998 A | 5/1991 | Cowan et al. |
| 5,083,408 A | 1/1992 | Blom et al. |
| 5,098,472 A | 3/1992 | Watkins et al. |
| 5,104,659 A | 4/1992 | Fishbein et al. |
| 5,116,414 A | 5/1992 | Burton et al. |
| 5,135,744 A | 8/1992 | Alexander et al. |
| 5,139,566 A | 8/1992 | Zimmerman |
| 5,178,495 A | 1/1993 | Cameron |
| 5,181,952 A | 1/1993 | Burton et al. |
| 5,201,925 A | 4/1993 | Itzel et al. |
| 5,270,108 A | 12/1993 | Savoy |
| 5,292,504 A | 3/1994 | Cardin et al. |
| 5,296,227 A | 3/1994 | Norval et al. |
| 5,317,834 A | 6/1994 | Anderson |
| 5,439,924 A | 8/1995 | Miller |
| 5,449,250 A | 9/1995 | Burton et al. |
| 5,492,696 A | 2/1996 | Price et al. |
| 5,525,147 A | 6/1996 | Dunstan et al. |
| 5,679,364 A | 10/1997 | Levy |
| 5,698,210 A | 12/1997 | Levy |
| 5,744,423 A | 4/1998 | Voris et al. |
| 5,747,519 A * | 5/1998 | Kodama et al. ............ 514/407 |
| 5,801,194 A | 9/1998 | Voris et al. |
| 5,846,553 A | 12/1998 | Levy |
| 5,856,271 A | 1/1999 | Cataldo et al. |
| 5,858,384 A | 1/1999 | Levy |
| 5,858,386 A | 1/1999 | Levy |
| 5,860,266 A | 1/1999 | Martinet et al. |
| 5,885,602 A | 3/1999 | Levy |
| 5,885,605 A | 3/1999 | Levy |
| 5,898,019 A | 4/1999 | Voris et al. |
| 5,902,596 A | 5/1999 | Levy |
| 5,902,597 A | 5/1999 | Iwakawa et al. |
| 5,925,368 A | 7/1999 | Voris et al. |
| 5,939,086 A | 8/1999 | Levy |
| 5,985,304 A | 11/1999 | Voris et al. |
| 6,001,382 A | 12/1999 | Levy |
| 6,060,076 A | 5/2000 | Voris et al. |
| 6,099,850 A | 8/2000 | Voris et al. |
| 6,183,825 B1 | 2/2001 | Crook |
| 6,224,957 B1 * | 5/2001 | Crook et al. ............. 428/36.91 |

| | | | |
|---|---|---|---|
| 6,319,511 B1 | 11/2001 | Voris et al. |
| 6,322,803 B1 | 11/2001 | Voris et al. |
| 6,331,308 B1 | 12/2001 | Voris et al. |
| 6,335,027 B1 | 1/2002 | Levy |
| 6,337,078 B1 | 1/2002 | Levy |
| 6,346,262 B1 | 2/2002 | Levy |
| 6,350,461 B1 | 2/2002 | Levy |
| 6,387,386 B1 | 5/2002 | Levy |
| 6,391,328 B1 | 5/2002 | Levy |
| 6,488,998 B1 | 12/2002 | Crook |
| 6,572,872 B2 | 6/2003 | Voris et al. |
| 6,803,051 B1 | 10/2004 | Voris et al. |
| 2002/0041892 A1 | 4/2002 | Voris et al. |

FOREIGN PATENT DOCUMENTS

| | | |
|---|---|---|
| AU | 23427/84 B | 8/1984 |
| AU | 48655/90 A | 8/1990 |
| AU | 62329/90 | 3/1991 |
| AU | 82443/91 B | 2/1992 |
| AU | 13886/95 B | 8/1995 |
| AU | 52454/96 A | 12/1996 |
| CA | 2 070 231 A1 | 12/1992 |
| DE | 1 929 314 A | 12/1970 |
| EP | 0 152 976 A | 8/1985 |
| EP | 0 286 009 A2 | 10/1988 |
| EP | 0 594 892 A1 | 5/1994 |
| EP | 0 582 823 B1 | 7/1999 |
| GB | 1494814 A | 12/1977 |
| GB | 2 018 593 A | 10/1979 |
| GB | 2 098 541 A | 11/1982 |
| JP | 52-72802 | 6/1977 |
| JP | 58-39601 | 3/1983 |
| JP | 58-113102 | 7/1983 |
| JP | 60-202801 A | 10/1985 |
| JP | 62-236937 | 10/1987 |
| JP | 64-58739 A | 3/1989 |
| JP | 1058739 A | 3/1989 |
| JP | 62-94165 A2 | 10/1994 |
| JP | 8302080 A | 11/1996 |
| SU | 1690654 A1 | 11/1991 |
| WO | WO 84/02447 | 7/1984 |
| WO | WO 90/14004 | 11/1990 |
| WO | WO 92/03927 | 3/1992 |
| WO | WO 95/18532 | 7/1995 |
| WO | WO 95/22902 | 8/1995 |
| WO | WO 96/28973 | 9/1996 |
| WO | WO 96/40849 | 12/1996 |
| WO | WO 97/47190 | 12/1997 |
| WO | WO 98/21960 | 5/1998 |
| WO | WO 99/41983 | 8/1999 |
| WO | WO 99/42264 | 8/1999 |
| WO | WO 00/37058 | 6/2000 |
| WO | WO 01/08485 | 8/2001 |
| WO | WO 02/035930 | 5/2002 |
| WO | WO 02/43487 | 6/2002 |
| ZA | 86/1133 | 2/1986 |

OTHER PUBLICATIONS

Burton et al., "A Controlled-Release Herbicide Device for Multiple-Year Control of Roots at Waste Burial Sites," *Journal of Controlled Release*, 8 pages (1986).
Chang et al., "Control of Ant Damage to Polyethylene Tubes Used in Drip Irrigation Systems in Hawaiian Sugarcane Fields," *International Society of Sugar Cane Technologists*, pp. 1686-1692 (Feb. 1-11, 1980).
Chen et al., "Approaches to the Improvement of Biological Resistance of Wood through Controlled Release Technology," *Proceedings of the 13th Int'l Symposium on Controlled Release of Bioactive Materials*, pp. 75-76 (Aug. 3-6, 1986).
Battelle Technology Transfer Bulletin, "Controlled-Release Chemicals for Inhibiting Plant Roots," 2 pgs (Dec. 1984).
Cline et al., "Biobarriers Used in Shallow Burial Ground Stabilization," *Nuclear Technology*, vol. 58, pp. 150-153 (1982).
Hughes, "Controlled Release Technology Inhibits Root Growth," *Controlled Release Business and Technology*, p. 15, 1989.
Jury et al., "Behaviour Assessment Model for Trace Organics in Soil: I. Model Description," *J. Environ. Qual.*, vol. 12, No. 4, pp. 558-564 (1983).
Jury et al., "Behaviour Assessment Model for Trace Organics in Soil: III. Application of Screening Model," *J. Environ. Qual.*, vol. 13, No. 4, pp. 573-579 (1984).
Jury et al., "Behaviour Assessment Model for Trace Organics in Soil: IV. Review of Experimental Evidence," *J. Environ. Qual.*, vol. 13, No. 4, pp. 580-586 (1984).
Burton et al., "Chapter 18: The Use of Controlled Release Herbicides in Waste Burial Sites," *Controlled Release Delivery Systems*, Marcel Dekker, NY (1983); pp. 291-300.
"Soil Fumigants are Remarkably Effective in Stopping Decay of Wood," *Chemical Week*, p. 39 (Sep. 25, 1974) (Abstract only).
Solie et al., "Simulation of Trifluralin Diffusion in the Soil," *Transactions of the ASAE*, pp. 1463-1467 (1984).
Steyaart, "Proceedings, Eighty-Second Annual Meeting of the American Wood-Preservers' Association: Address," *Crossties*, vol. 68, No. 3, pp. 45-46 (Mar. 1987).
Streile, "The Effect of Temperature on Pesticide Phase Partitioning, Transport, and Volatilization from Soil," *Abstract of the Dissertation*, 37 pages (1984).
Van Voris et al., "Long-Term Controlled Release of Herbicides: Root-Growth-Inhibiting Biobarrier Technology," pp. 1-19; submitted 1988.
Probst et al., "Fate of Trifluralin in Soils and Plants," *J. Agric. Food Chem.*, vol. 15, No. 4, pp. 592-599 (Jul.-Aug. 1967).
Delcourt et al., Abst., *Cytologia*, vol. 41, No. 1, pp. 75-84 (Jan. 1976) (Summary on p. 83).
Lignowski et al., "Trifluralin and Root Growth," *Plant and Cell Physiology*, vol. 76, pp. 701-708 (1972).
Chemical Abstracts, vol. 88, 154553m, p. 1177 (1978) (abstract).
Database WPI / Derwent abstract, Section CH Week 8547, Derwent Publications, London GB Class A97, Nihon Tokushu Noyaku Seizo KK abstract No. 85-293614 of JP 60-020801 A (Oct. 1985).
Baker and Lonsdale, "Controlled Delivery—An Emerging Use for Membranes," *Chemtech*, pp. 668-674 (Nov. 1975).
Burton et al., "Application of Controlled Release Technology to Uranium Mill Tailings Stabilization" presented at American Nuclear Society Topical Meeting on Waste Management, Tucson, Arizona, pp. 1009-1021 (Feb. 23-26, 1981).
Burton et al., "A Controlled-Release Herbicide Device For Multiple-Year Control of Roots at Waste Burial Sites," 10th International Symposium on Controlled Release of Bioactive Materials, San Francisco, California, pp. 305-308 (Jul. 24-27, 1983).
PNL-3000-6 Nuclear Waste Management Quarterly Progress Report, Apr. through Jun. 1980 prepared for the U.S. Department of Energy under Contract DE-AC06-76RLO 1830, pp. 22.1 and 22.2, "Application of Long-Term Chemical Biobarriers for Uranium Tailings" (Sep. 1980).
Kumar et al., "The Effect of Wood Preservatives on Physical Properties of Wood, Pt. 3. Effect of Some Emulsion Additives and Post Treatments on Shrinkage-Swelling and Water Repellency of Copper-Chrome-arsenic Treated Wood" *Journal of the Timber Development Association of India*, vol. 23, No. 3, pp. 9-13 (Jul. 1977).
Chemical Abstracts, vol. 89, 158777f (1978) (abstract of French Patent No. 2,358,831).
The Agrochemicals Handbook, 2nd Ed., D. Hartley, ed. The Royal Society of Chemistry, 39 selected pages (1987).
The Pesticide Manual: A World Compendium, 8th Ed., C. Worthing, Ed., British Corp Protection Council, 1987, pp. 7179-7180. (Table of Contents and 146 selected pages).
Chemical Abstracts, vol. 88, 75506V (Prevention of Shipworms on Wood Stored in Seawater).
Morrell, J., Woodpole Conference Proceedings, Portland, Oregon, 101 pages Mar. 10-11, 1986.
Hayes, W.C., "Extending Wood Pole Life: Solving a $5 Billion a Year Program," *Electrical World*, pp. 41-47 (Feb. 1986).

Shepherd, M., "Managing America's Wood Pole Inventory," *EPRI Journal*, vol. 12, No. 6 11 pages (Sep. 1987).

Zabel, R. et al., The Fungal Associates, "Detection, and Fumigant Control of Decay in Treated Southern Pine Poles," Final Report EL-2768 for EPRI Research Project 47191, State University of New York (Dec. 1982) (Table of Contents and 95 selected pages).

Graham et al., "Controlling Biological Deterioration of Wood with Volatile Chemicals," EPRI Report EL-1480, Oregon State University (1980).

Dickinson et al., "Boron as a Preservative Against Internal Decay," *Distrib. Dev.*, vol. 89, No. 1, pp. 9-14 (Mar. 1989).

Zahora et al. "Gelatin Encapsulation of Methylisothiocyanate for Control of Wood-Decay Fungi", *Forest Products Journal*, vol. 35 (7/8) pp. 64-69 (1985).

Groundline Repair for Wood Poles, *EPRI Journal*, 6 pages (Apr./May 1986) vol. 11, No. 3.

N.N. Mel'nikov, Chemistry and Technology of Pesticide, Moscow, Khimiya, p. 26 (1974) (translation).

A. Pajak et al., "Morphological and Cytological Effects Brought About By Trifluralin on Pea (Pisum Sativum L.)," *Biuletyn Warzywniczy*, pp. 451-462 (1979) (abstract provided as first page).

Y. Eshel et al., "Effect of Dinitroanilines on Solanaceous Vegetables and Soil Fungi," *Weed Science*, pp. 243-246, vol. 20, Issue 3 (May 1972).

Termfilm Termigranuls, "The Anti Termite Solution", by Cecil Co., 5 pages (Oct. 18, 1996).

P. Van Voris et al., "Long-Term Controlled Release of Herbicides Root-Growth Inhibition", Chapter 18 from the American Chemical Society Symposium Series, pp. 222-240, 1988.

Eshel et al., Chem. Abst. vol. 77 (1972), 71309h.

Pajak et al., Chem. Abst., vol. 94 (1981) 133986p.

Termite Resistant Sheet for Moisture Permeable Building Material Obtained by Adding Anti-Termite Agent Into Laminated Sheet Obtained by Laminating Nonwoven Fabric or Woven Cloth onto Porous Polyolefin Sheet, 01058739/PN Mar. 6, 1989 (Abstract).

\* cited by examiner

MULTI-LAYER BARRIER PREVENTING WOOD PEST ACCESS TO WOODEN STRUCTURES

CROSS REFERENCE TO RELATED APPLICATION

The present application is a divisional of U.S. application Ser. No. 09/353,494 filed Jul. 13, 1999 now U.S. Pat. No. 6,803,051, which is a continuation of U.S. application Ser. No. 09/030,690 filed Feb. 25, 1998, now U.S. Pat. No. 5,985,304.

FIELD OF THE INVENTION

The present invention relates to barriers for preventing wood pest (e.g. termite and boring insect) access to wooden structures for the long-term protection of wooden structures. More particularly, it relates to a composition and method which creates and maintains an exclusion zone for insect pests such as termites, ants and other boring insects. As used herein, the term "bioactive" means stimulating an organism, usually in a negative way up to and including death for purposes of a deterrent.

BACKGROUND OF THE INVENTION

Wood which is in contact with concrete, such as in wooden building construction and wood which is in contact with soil for example fence posts, utility poles, railroad cross-ties and wooden supports, can be structurally degraded by the action of termites, ants and other boring insects. Insecticides are available to protect wood from the action of such pests.

In wooden building construction, wood in contact with concrete may be structurally degraded by action of one or more wood pests including but not limited to termites, ants and other boring insects. Present methods of preventing or retarding the advance of insects includes fumigation wherein the entire structure may be sealed and an insecticide released therein. Disadvantages of this method include ecological and human health concerns as well as the limited time until the fumigant is sufficiently reduced in concentration to permit insect ingress.

Although insecticides are effective against the action of the boring insects, the insecticides must be repeatedly applied at intervals of from a few days to a few months or a year to remain effective. If insecticides are applied by themselves in sufficient quantity to be effective over a period of time, they pose ecological concerns, human health, and may present unpleasant odors, soil leaching and volatility of the insecticide. Furthermore, even the greatest amounts of insecticides applied by themselves dissipate within a relatively short time and need to be reapplied.

A further disadvantage of conventional application methods is that the concentration of bioactive ingredients resulting from a single application of insecticide starts out well above the minimum level necessary for effectiveness, but decreases rapidly and within a relatively short period of time drops below the minimal effective level necessary to maintain a barrier.

To this end, a number of techniques for the controlled release of chemicals such as insecticides have been developed in recent years. These methods employ polymer matrices and microcapsules to release insecticide.

Cardarelli U.S. Pat. No. 4,400,374 discloses the use of polymer matrices generally made of polyethylene, polypropylene, ethylene vinyl acetate, polyamide, polystyrene, polyvinyl acetate, or polyurethane to control the release of insecticides such as the insecticide commercially available under the tradename Dursban. The polymer matrices disclosed in U.S. Pat. No. 4,400,374, incorporate porosigen and a porosity reducing agent which upon contact with soil moisture or an aqueous environment dissolves the matrix.

Similarly, Cardarelli U.S. Pat. No. 4,405,360 relates to a polymer release matrix which can be composed of polyamide, polyurethane, polyethylene, polypropylene, polystyrenes and other polymers. The control release mechanism works in combination with a porosigen to release a herbicide in a moist environment.

A disadvantage of the Cardarelli methods is the necessity of sufficient moisture to dissolve the matrix. Periods of dryness, while extending the life of the matrix, would result in a decrease in the insecticide concentration thereby permitting access to the insects. In addition, the longevity of the matrix is variable and dependent upon moisture content.

In addition, Wysong U.S. Pat. No. 4,435,383 teaches the use of a controlled release mechanism for insecticides including carbamates, organothiophosphates, organophosphates, perchlorinated organics and synthetic pyrethroids. The release mechanism comprises a hydrophobic barrier monomer namely styrene and/or methyl styrene in combination with a monomer selected from one or more unsaturated mono- or di-carboxylic acids.

Another reference, Tocker U.S. Pat. No. 4,282,209 discusses a process for the preparation of insecticide-polymer particles. The insecticide, methomyl, is used to control insects which attack a tobacco, cotton or agricultural crops. Methomyl is dissolved with polymers such as polyamides, urethanes and epoxies to provide extended residual insecticidal activity.

A second Tocker patent, U.S. Pat. No. 4,235,872, discloses the use of slow-release insecticide microcapsules having a core of methomyl surrounded by a cover of allaromatic, uncrosslinked polyurea. In the arrangement disclosed in this patent, methomyl is used to protect vegetables, field crops and fruit crops.

A sixth reference, Young et al. U.S. Pat. No. 4,198,441, discloses the use of insecticides such as Dursban in a controlled release matrix comprising an organopolysiloxane, a hydrolyzable silane and a hydrolyzable organic titanium.

Additionally, Young et al. U.S. Pat. No. 4,160,335 discloses a mode of dispersing insect control substances by applying stripes to sheets of cellophane. The insect control substance which can include Dursban is placed in a polymer as well.

Another method is described in an Australian patent AU-B-82443/91. In this patent, there is described two sheets of plastic drawn from supply rolls. The upper face of the lower sheet and the lower face of the upper sheet are drawn past respective coating rollers which apply a coating of pesticide (e.g. permethrin) in a volatile solvent to the faces of the sheets. The coated faces of the sheets are brought together by passing them between compressive rollers. The coated and pressed sheets are laid under building foundations, or placed around trees or plants to prevent termite attack. Disadvantages of this product and method include (1) severance of a layer permits rapid escape of the coating, and (2) the coating is not integral to the sheets thereby permitting faster diffusion through the sheets and limiting the effective life.

Coated granules have a pesticide absorbed onto a matrix such as clay and then coated with cross-linked resins which helps slow the release rate. Clay loses or releases pesticide over a short period of at most a few weeks.

Although the prior art does disclose the use of an insecticide incorporated into, a polymer matrix as controlled release agents, none of the references teach the creation and maintenance of a completely effective exclusion zone lasting several years or more. It is desirable to create a zone so as to prevent any contact between the wood structure and insects capable of damaging such structures. A reliable exclusion zone is necessary to protect wood structures for periods of time substantially greater than one year.

Therefore, in view of the above, it is an object of this invention to provide a zone of insecticide to protect wooden structures. Such zone consisting of a long term low volatility barrier and a high volatility short term barrier to protect soil.

It is a further object of this invention to maintain an exclusion zone for relatively great lengths of time of about 10 to 20 years.

SUMMARY OF THE INVENTION

The present invention is a wood pest barrier having a lifetime that is effective over the life of the structure. The lifetime is achieved by binding the pesticide within the polymer matrix thereby substantially preventing release of the pesticide from the polymer. Binding may be achieved by mixing the pesticide with a carrier as a bound friable mix prior to placing the bound friable mix within the polymer matrix.

The barrier may be supplemented with additional layer(s) including but not limited to scrim, mesh, sheet, and combinations thereof. The additional layer(s) may contain a second pesticide that is the same or different compared to the pesticide in the barrier. In addition, the second pesticide may be permitted to release from the additional layer(s) for enhanced short term protection.

The barrier and/or additional layer(s) are made with a polymer selected from the group consisting of thermoplastic polymers, thermoset polymers, elastomeric polymers and copolymers thereof. By incorporating the insecticides into the polymers, the insecticides can be held or released at such a rate that they will continue to be effective as toxicants or repellents for insects capable of damaging wood structures for a prolonged period of time while at the same time maintaining sufficient concentrations within the barrier to prevent insect penetration through the barrier.

According to one aspect of this invention, there is provided a polymeric-carrier system wherein the pesticide is bound to the carrier as a bound friable mix. The sheeting with the bound friable mix is then placed near a wooden structure to provide a barrier that wood pests do not penetrate. An additional layer may provide means for a slow and relatively constant release of the volatile insecticide in order to create a barrier zone beyond the barrier itself in the soil around a wood structure. The polymers include thermoplastic polymers, thermoset polymers, elastomeric polymers as well as copolymers thereof and the insecticide comprises the family of insecticides known as pyrethrins.

According to another aspect of this invention, an exclusion zone is created by placing an extrusion near the wooden structure to be protected. The extrusion has a polymeric delivery system capable of controlled release of the insecticide. The carrier system maintains a steady and effective concentration of insecticide in the exclusion zone for great lengths of time.

According to another aspect of this invention, a pellet comprising a polymer and insecticide is provided to create and maintain an equilibrium concentration of insecticide for ants, termites and other wood boring insects in an exclusion zone for the wooden structure. The pellet is placed near a wooden structure to treat the soil in order to shield the wooden structure from termites, ants and other boring insects. The pellet can be placed near the structure by a variety of means. Additionally, the pellet can be embedded in a board or even included in a foam. In preferred embodiments the polymers include thermoplastic polymers, thermoset polymers, elastomeric polymers as well as copolymers thereof and the insecticide are pyrethrins.

According to another aspect of this invention, an exclusion zone is created by injecting a hot melt polymeric mixture. The controlled release device comprises one or more pyrethrins and the polymer is selected from the group consisting of thermoplastic polymer, elastomeric-polymers and copolymers thereof.

According to further aspects of the invention, temperature driven controlled release devices are used to provide the exclusion zones.

According to another aspect of this invention, the controlled release device is used to fumigate structures.

It is desirable to place a barrier or create a zone so as to prevent any contact between the wood structure and insects capable of damaging such structures. An exclusion zone is necessary to protect wood structures for extended periods of time.

In a further aspect of the present invention a high density polymer having a low volatility insecticide providing a low release rate of insecticide is combined with a low density (soft) polymer having a more volatile insecticide to provide a reliable exclusion zone.

Therefore, in view of the above, it is an object of this invention to provide a barrier of insecticide to protect wooden structures.

It is a further object of the present invention to provide a barrier and an exclusion zone having of a long term low volatility barrier and a high volatility short term barrier to protect adjacent soil.

It is a further object of this invention to maintain a barrier for relatively great lengths of time or about 10 to 20 years.

The present invention, together with attendant objects and advantages, will be best understood with reference to the detailed description below read in conjunction with the accompanying drawing.

DETAILED DESCRIPTION

Figure 1:
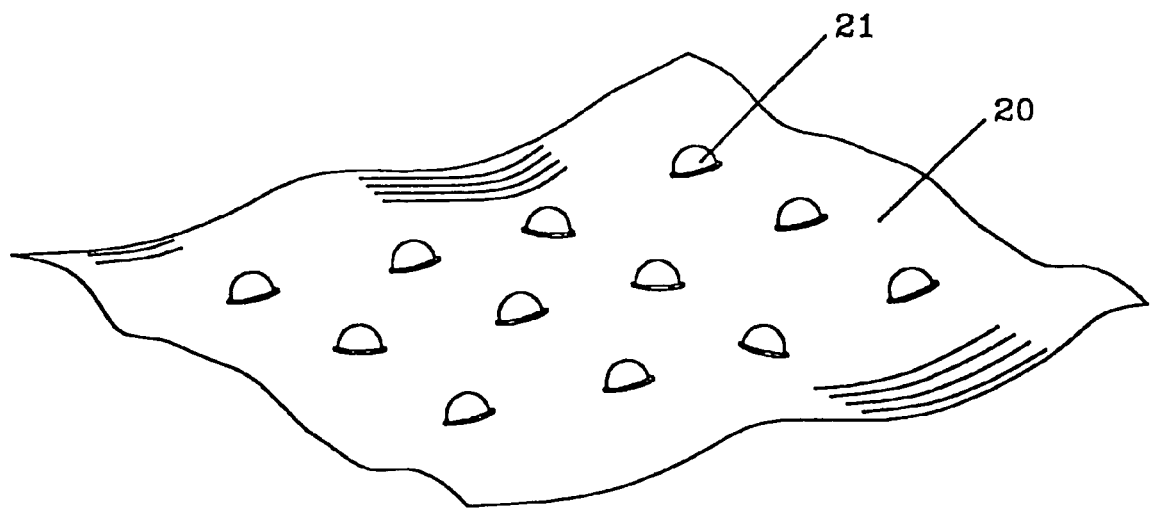
FIG. 1 illustrates a first embodiment of the invention, comprising spun-bonded polymeric sheeting, and a physical melt-bonded mixture of polymer and insecticide, wherein the mixture of polymer and insecticide is bonded in spots to the polymeric sheeting.

It has been found that there is a significant reduction of insects capable of damaging wood structures when a barrier alone or in combination with an exclusion zone of insecticide is maintained for great lengths of time in the soil surrounding such structures. An exclusion zone is a zone having a sufficient amount of chemical agent to deter fauna. In the present invention, the chemical agent is an insecticide and the fauna are insects especially boring insects, for example termites and ants. According to the present invention, the insecticide is held in a barrier and/or is released from a controlled release device comprising a polymer matrix system will last for at least 6 years.

A controlled release device refers to an apparatus that results in controlled and sustained release of an bioactive chemical to its surface and from its surface into a surrounding medium, for example soil. The apparatus provides a method for controlled release of the chemical into the surrounding environment. The device releases insecticide at a high rate initially and a lower, steady rate thereafter. This release profile assures that the wooden object becomes protected in a relatively short period of time and that, subsequent to reaching the minimum effective level only the amount of insecticide necessary to replace the degraded insecticide is released. This release profile diminishes potential environmental and health problems of the treatment and reduces the cost of the treatment. The apparatus release rate is dependent only upon the apparatus construction and is independent of external elements such as water.

The controlled release device provides a near to midterm solution by releasing the insecticide into the soil at a desired rate to create a zone having the "minimal effective level" of insecticide necessary to prevent insect intrusion. As used in this specification and the appended claims, the term "minimal effective level" is defined to mean the level of insecticide needed in the zone to prevent insects from entering the zone, the specific level depends on the specific insect and the specific insecticide. When placed adjacent to a foundation or below-grade structural portion, the exclusion zone is created in the soil near the apparatus. When placed between a non-wood structural portion and an attached wood structural portion, the exclusion zone is created at the interface between the non-wood structural portion and the attached wood structural portion.

The insecticides used in preferred embodiments should be U.S. Environmental Protection Agency approved insecticides to kill or repel termites, ants and other boring insects. The insecticide which is presently preferred for use in the present invention are pyrethrins, including tefluthrin, lambdacyhalothrin, cyfluthrin and deltamethrin. It will, however, be recognized by those skilled in the art that other effective insecticides such as isofenphos, fenvalerate, cypermethrin, permethrin and natural pyrethrin can also be used. These are available from a number of commercial sources such as Dow, Mobay, ICI, Velsicol and FMC respectively. A combination of insecticides, or one or more insecticides in combination with other bioactive ingredients such as fungicides is also in accord with this invention.

A first controlled release embodiment of the invention, is illustrated in FIG. 1, utilizes a polymeric-carrier apparatus for the controlled release of insecticide to generate an exclusion zone. The embodiment comprises spun-bonded polymeric sheeting 20, and a physical melt-bonded mixture of polymer and insecticide (shown as spots 21 in FIGS. 1 and 3-5). The spun-bonded polymeric sheeting 20 can be either a woven or non-woven textile or it can be a polymeric sheet. Such textiles can be obtained from a number of manufacturers such as Reemay, Exxon Fibers and Phillips Fibers. Preferably, the textile is woven or non-woven polypropylene.

The polymer in the melt-bonded mixture can comprise any number of thermoplastic polymers, thermoset polymers, elastomeric polymers or copolymers thereof. The selection of the polymers depends upon the desired release rate, the compatibility of the polymer with insecticide and upon environmental conditions. By way of example and not intending to limit the scope of this invention, the following polymers can be used: high density polyethylene, low density polyethylene, vinyl acetate, urethane, polyester, santoprene, silicone, or neoprene. However, the preferred polymers are high density and low density polyethylene. Although the above-mentioned insecticides can be used for best results, the insecticide should ideally comprise chlorpyrifos.

The mixture of polymer and insecticide may be placed on the spun-bonded polymeric sheeting in spots. These spots should be spaced so as to adequately maintain the amount of insecticide above the minimal effective level in an exclusion zone. The minimal effective level is the least amount of insecticide needed in a zone so as to prevent intrusion by insects. Spots 21 in FIGS. 1 and 3-5 are preferably about 0.5 to 1.5 centimeters in diameter, and about 0.5 to 1.5 centimeters in height. The size and shape of the spots will depend upon the user's preference and can be tailored to the job contemplated by the buyer. The spots 21 can be configured in rows with the spacing of the spots preferably being from about 1.5 to 4 centimeters from adjacent spots. It will be recognized by those skilled in the art that other configurations of spots can also be used depending on the particular application. The insecticide releasing polymeric sheet is placed near or around the wooden structure to create an exclusion zone by the controlled release of insecticide.

A second controlled release embodiment of the invention also utilizes a polymeric-carrier delivery system for the controlled release of insecticide comprising spun-bonded polymeric sheeting 20 and a physical melt-bonded mixture of polymer and insecticide. The polymeric sheeting 20 as in the first embodiment can be either woven or non-woven polypropylene upon which is bonded the physical melt-bonded mixture (shown as stripes 22 in FIG. 2). Similarly, the polymers and insecticide described above with respect to the first embodiment may also be used in the embodiment described in this section.

Figure 2:
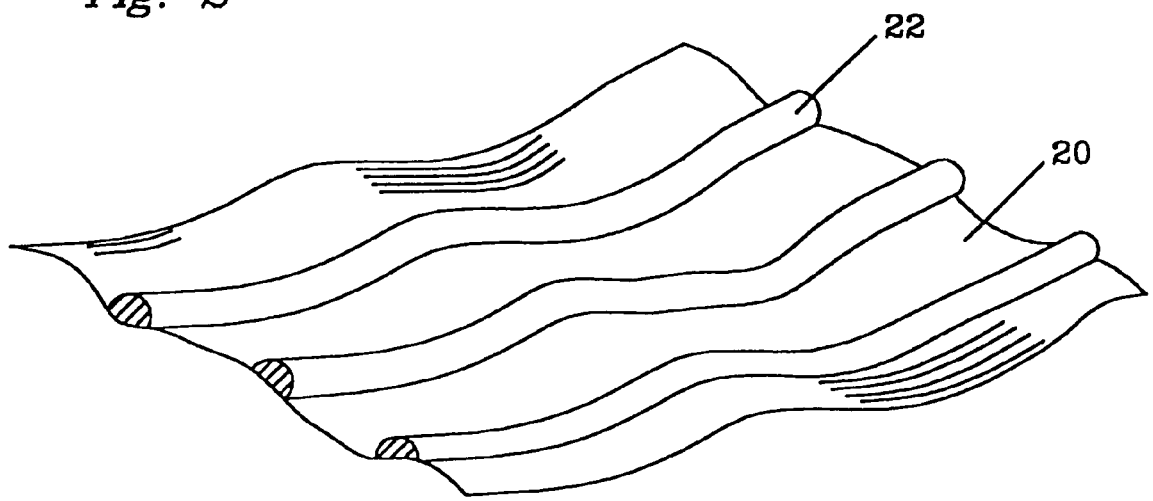
FIG. 2 illustrates a second embodiment of the invention, comprising spun-bonded polymeric sheeting, and a physical melt-bonded mixture of polymer and insecticide, wherein the mixture of polymer and insecticide is bonded in stripes to the polymeric sheeting.

The mixture of polymer and insecticide of the second embodiment may alternatively be placed on spun-bonded polymeric sheeting using extruder systems which provide stripes, e.g., as shown in FIG. 2. The stripes 22 can be about 1 centimeter in height, and about 5 to 15 centimeters apart. Optimally the stripes should be placed about 10 centimeters apart. It is desirable that the stripes should be configured in such an arrangement so as to permit a steady state concentration of insecticide in the exclusion zone after an initial burst of insecticide. After the stripes are applied to the polymeric sheet, the sheet is placed on or near the wooden structure to be protected from insects.

Binding filler and/or carriers may also be included in all of the embodiments of the invention. The inclusion of the binding filler and/or carrier permits greater amounts of insecticide for a given release rate or permits a lower release rate for a given amount of pesticide. The binding carrier binds the pesticide. Binding carriers found to bind the pesticide include carbon based carriers for example carbon black, activated carbon and combinations thereof. It is believed that alumina, silicoaluminate, hydroxyapatite and combinations thereof may be comparable to carbon for binding bioactive chemicals.

When a carbon based carrier is utilized, the first step is to insure dryness of the carbon followed by mixing the insecticide in a liquid form with the carbon. Only sufficient carbon black (filler) is used to produce a friable mixture. The term "friable" means substantially dry or non-sticky flowable particles. Certain pesticides may have to be heated to achieve a liquid form. The liquid insecticide adheres or binds to the extremely large surface area of the finely divided carbon black and the mixture is cooled for incorporation in the polymer. Polymers which may be used in a carbon application are a polyethylene, polypropylene, copolymers or blends of polyethylene and polypropylene, polybutylene, epoxy polymers, polyamides, acrylate-styrene-acrylonitrile, aromatic or unsaturated polyesters, polyurethanes, silicones, or any other suitable polymers or copolymers thereof.

The carbon-insecticide mixture in the first and second embodiments (or just insecticide, if carbon is not used) is then mixed with the polymer, preferably polyurethane, in either the molten, powder or liquid stage. Next this mixture is bonded to the polymeric sheeting. In the first and second embodiments of the invention, the polymer and insecticide are melt-bonded to the polymeric sheeting.

Another mode of bonding the mixture of polymer and insecticide to the polymeric sheeting is by "through-injection molding", a technique which is known in the art. In "through-injection molding", molten material is injected from a heated nozzle through a porous web and into a mold. The molten material flows through the web under pressure and is solidified in the mold. While the molten material is being injected, the porous web allows air to escape, but it also retains the molten mass under pressure until it has cooled.

A different method of bonding the mixture of polymer and insecticide to the polymeric sheeting is by placing a melted mixture of polymer and insecticide on the spun-bonded polymeric sheeting. If the mixture is melted, it must be allowed to cool, cure and solidify. As used hereinafter, "a melted mixture of polymer and insecticide" is intended to indicate that the polymer is either melted or already in the liquid stage. The insecticide may also be melted or contained in a slurry solution, depending on its melting point. A "melted mixture of polymer and insecticide" can also contain carbon or other additives which do not melt but flow with the melted polymer/insecticide mass.

The first and second embodiments of the invention should provide release rates sufficient to maintain an effective insecticide concentration in the exclusion zone to kill or repel insects but at sufficiently slow rates to maintain an effective concentration for an extended period of time.

Overall, a preferred composition for the first and second embodiments of the invention comprises from about 70 to 95 parts by weight of carrier polymer, from about 0 to 15 parts by weight of carbon, and from about 5 to 30 parts by weight of insecticide. The design considerations of the controlled release devices vary according to such factors as user preference and geographic conditions. The steady state release rate of the polymeric delivery system of these two embodiments after the initial burst of insecticide can be maintained for at least 6 years as a barrier to insects such as ants and termites. However, the equilibrium concentration of this embodiment can easily be adjusted to meet the specific needs of each user.

Optionally, the embodiments shown in FIGS. 1-5 may comprise a pesticide-impervious sheet (not shown) such as a metallized foil. The metallized foil or an extruded sheet of a polymer is laminated to one side of the spun-bonded polymeric sheeting in order to direct the flow of insecticide.

A further embodiment of the present invention is a barrier of a pest-impervious sheet wherein a bound friable mix of the bioactive chemical or pesticide with a carbon carrier is placed within a polymer and exhibits substantially no release of the bioactive chemical. Substantially no release is defined as a release rate less than 0.4 $\mu g/cm^2/day$, preferably less than 0.1 $\mu g/cm^2/day$, and most preferably less than 0.05 $\mu g/cm^2/day$. This embodiment encompasses a release rate of 0.0 or below detectable limits. In this embodiment, pests are deterred upon "sniffing" or "scratching" a polymer surface and detecting the presence of the pest harmful bioactive chemical. Life time of the barrier is much longer than a barrier with a higher release rate. Moreover, a flaw or tear in the polymer will be less prone to "leak" bioactive chemical. Hence, two or more layers of this embodiment may be preferred to maintain a complete barrier. Multiple layers would permit a tear or hole in one layer but a pest would not pass a second or subsequent untorn layer. It may further be desirable to place a protective layer, for example scrim, on one or both sides of a barrier layer to avoid tearing.

Figure 3:
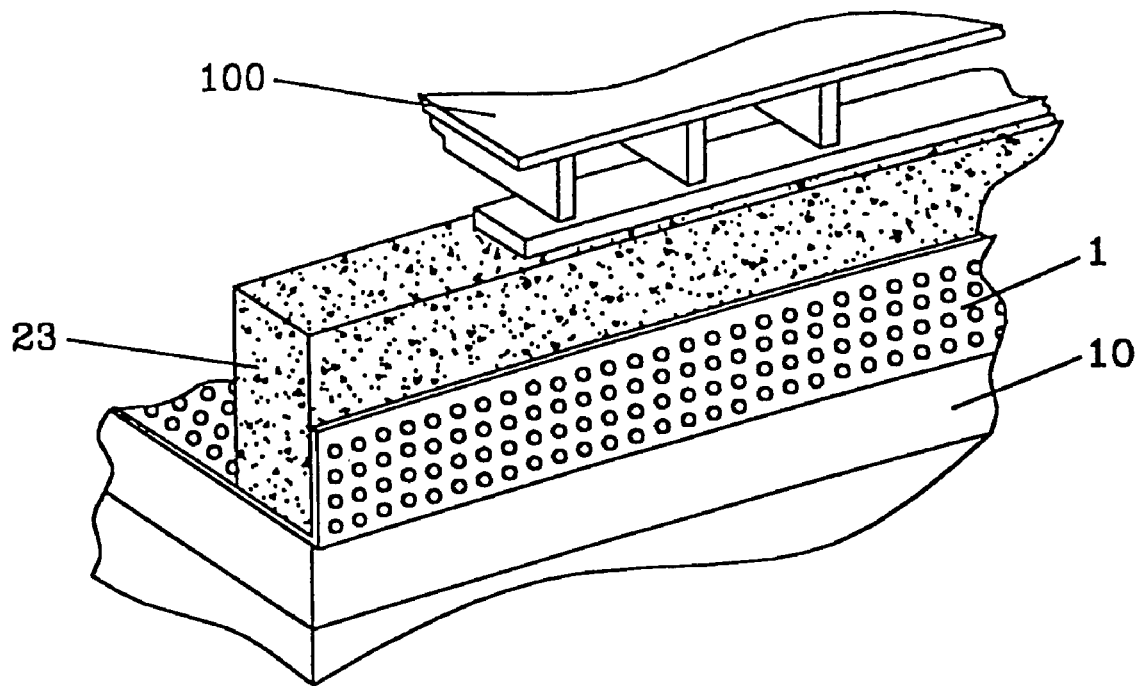
FIG. 3 illustrates a first manner of using the embodiments of the invention shown in FIGS. 1 and 2 and the exclusion zone created by the release of insecticide.
Figure 4:
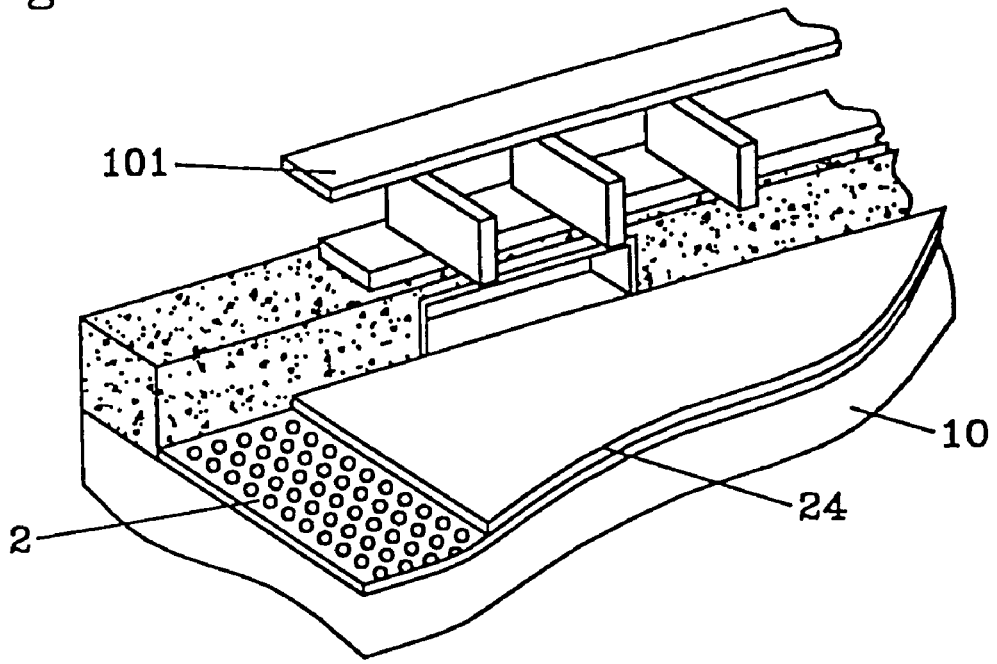
FIG. 4 illustrates a second manner of using the first and second embodiments of the invention to create an exclusion zone.
Figure 5:
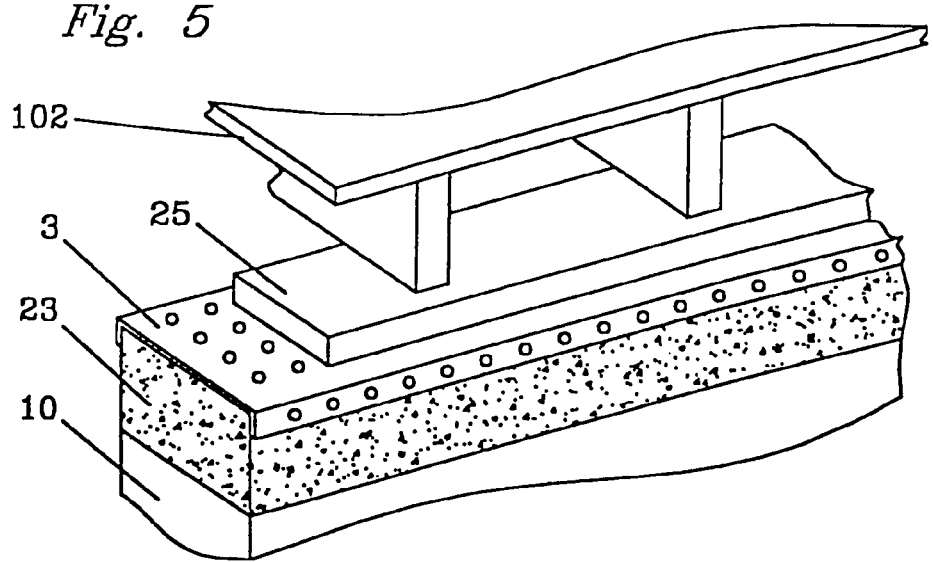
FIG. 5 illustrates a third manner of using the embodiments of the invention shown in FIGS. 1 and 2 creating an exclusion zone.

Once made, the polymeric-carrier delivery systems of the first and second embodiments are placed near the structure desired to be protected from insects. FIGS. 3-5 illustrate various applications of either the spotted or striped sheet embodiments of the invention. The FIG. 1 configuration is shown in FIGS. 3-5, but it is understood that the FIG. 2 configuration, or other configurations can work as well.

In FIG. 3, the polymeric-carrier delivery system 1 is placed under and alongside a concrete foundation 23 of a wooden structure 100 creating an exclusion zone 10 to protect the structure from termites, ants and other boring insects.

In FIG. 4, the polymeric-carrier delivery system 2 is placed under a structural member 24, such as a porch, patio, sidewalk, or under a basement foundation beside the wooden structure 101 to provide an exclusion zone 10.

In FIG. 5, the polymeric-carrier delivery system 3 is placed over and on the sides of the concrete foundation 23 of a wooden structure 102, but under the wooden portion 25 of the structure to create an exclusion zone.

Figure 6:
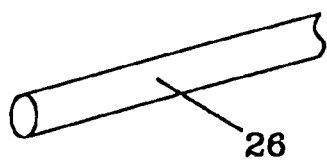
FIG. 6 illustrates a third embodiment of the invention, in the form of a cylindrical extrusion.
Figure 7:
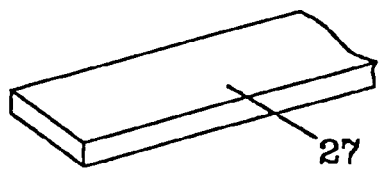
FIG. 7 illustrates a fourth embodiment of the invention, in the form of a flat strip extrusion.

Another embodiment of the invention is illustrated in FIGS. 6 and 7. This embodiment pertains to extrusions, such as extruded flexible cylinders 26 and extruded flexible flat strips 27 shown respectively in FIGS. 6 and 7. A wide variety of polymers which can be classified into four broad subgroups can be utilized. The groups include thermoplastic polymers, thermoset polymers, elastomeric polymers and copolymers of the three groups named above. By way of example, some polymers which can be used from the four groups are: high density polyethylene, low density polyethylene, EVA, vinyl acetate, urethane, polyester, santoprene, silicone, neoprene and polyisoprene. The preferred insecticide is chlorpyrifos although the insecticides described above can be used. A filler may also be added.

Cylinders preferably have a size ranging from about 5 to 15 millimeters in diameter, but most preferably about 10 millimeters in diameter for the optimal steady state delivery of insecticide into the exclusion zone. Flat strips should preferably have a thickness of from about 1 to 6 millimeters and a width of from about 5 to 15 millimeters. It, however, should be noted that both cylinders and flat strips can be designed to meet the varying conditions encountered by user.

Overall, in order to maintain an equilibrium concentration of pesticide in the exclusion zone for an extended period of time, the composition of this embodiment of the invention, should comprise from about 70 to about 95 parts by weight of polymer, from about 0 to about 30 parts weight of carbon, and from about 5 to about 30 parts by weight of pesticide. The composition of the extrusion can, however, be tailored to the specific needs of the user. It is estimated that the exclusion zone can be maintained for at least 6 years for a cylinder and likewise for flat strips.

Figure 8:
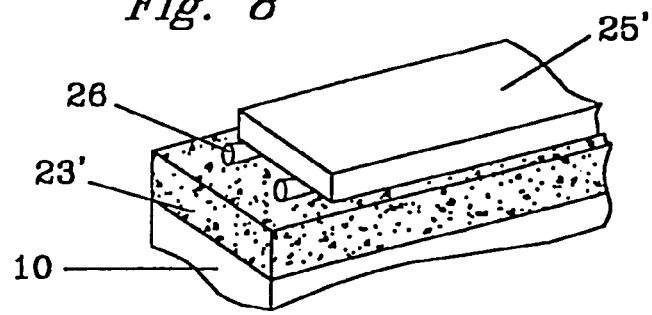
FIG. 8 illustrates a manner of creating an exclusion zone using the embodiment of the invention shown in FIG. 6.

The extrusions can be positioned in a variety of positions to create exclusion zones. FIG. 8 illustrates a manner of using the extrusion shown in FIG. 6. One or more flexible cylinders 26 are placed between the concrete foundation 23' and the wooden portion 25' of the structure. The flexible cylinders 26 release insecticide at a controlled rate to create an exclusion zone. An advantage of this configuration is that flexible cylinders 26 can be placed under a structure that has already been built. Similarly, in a manner not shown, the flexible cylinders can be placed vertically into the ground as opposed to horizontally. As will be recognized by those skilled in the art, the extrusions may have other suitable shapes and be placed in any suitable position depending upon the particular use contemplated.

Figure 9:
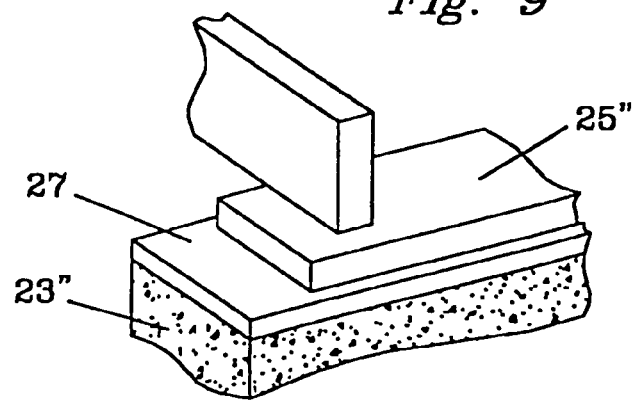
FIG. 9 illustrates a manner of using the embodiment of the invention shown in FIG. 7 to create an exclusion zone.

FIG. 9 illustrates a manner of using the flexible flat strip extrusion shown in FIG. 7. One or more flexible flat strips 27 create an exclusion zone by being placed between or alongside the concrete foundation 23" and the wooden portion 25" of the structure. The flexible flat strips 27 can also be placed vertically alongside a wall in an embodiment not illustrated in the drawings. Again, any suitable placement of the flat strips is considered as being within the scope of the invention.

The controlled release of insecticide can also be conveniently achieved by using pellets as illustrated in the embodiments shown in FIGS. 10-13. The pellet 13 comprises polymer, insecticide and preferably also includes a filler. Various polymers can be used in this embodiment. They can comprise polymers of four subgroups consisting of thermoplastic polymers, thermoset polymers, elastomeric polymers and copolymers thereof. Polymer selection from these four subgroups depends upon design considerations with the preferable polymer being either high density polyethylene or low density polyethylene. In turn, the insecticide preferable comprises tefluthrin, but the following insecticides can also be used: isofenphos, fenvalerate, cypermethrin, permethrin and other pyrethrins. For optimal results, a carrier such as carbon, can also be incorporated into the mixture.

The pellet 31 releases insecticide at a controlled rate for an extended period of time in order to establish an exclusion zone. The composition for such a pellet needed for the maintenance of a zone in the soil is from about 70 to about 95 parts by weight of polymer, from about 0 to about 30 parts by weight of carbon black, and from about 5 to about 30 parts by weight of insecticide. Ultimately, the compositions of the pellet depend upon user preference.

The pellets can be any convenient size depending upon the intended use, such as 1 to 25 millimeters in diameter (or width and thickness, if rectangular) by 2 to 20 centimeters or more in length. Furthermore, in order to fit specific user needs, the dimension of the pellets and the concentrations of the insecticide can easily be adjusted. However, an exclusion zone can be maintained for at least 6 years.

Figure 10:
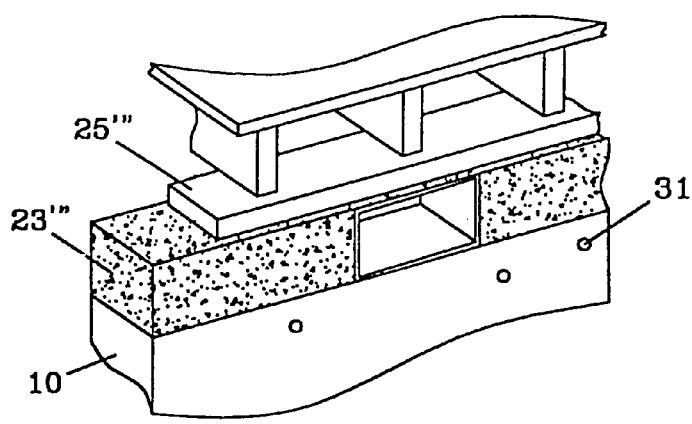
FIG. 10 illustrates another embodiment of the invention in the form of pellets wherein the pellets are being inserted into the ground near a wooden structure.
Figure 11:
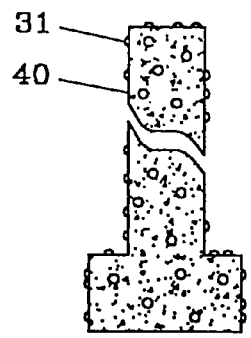
FIG. 11 illustrates a cross-sectional view of pellets placed on a surface.

Additionally, pellets 31 have the advantage that they can be conveniently placed most anywhere. The pellets of this embodiment of the invention are shown in FIG. 10. A pellet 31 is inserted near a wooden structure 25. The pellets as illustrated in FIG. 10 can be placed under a cement foundation 23''' or they can be placed directly under the wood structure (not illustrated) so as to permit the creation of a zone 10 surrounding the wooden structure 25''' to exclude insects capable of damaging such structures. FIG. 11 shows a cross-sectional view of pellets 31 inserted on a surface 40.

Figure 12:
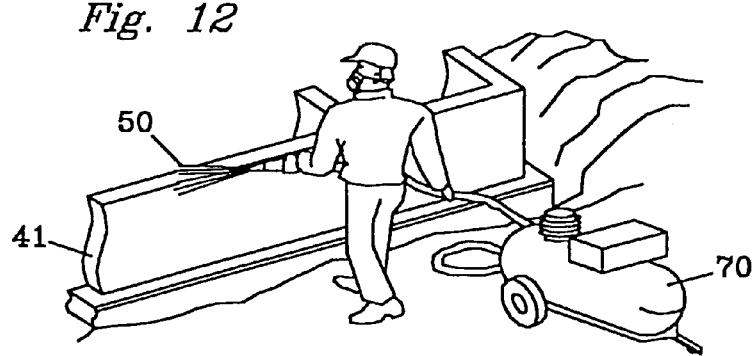
FIG. 12 illustrates the application of pellets to a concrete structure utilizing foam.
Figure 15:
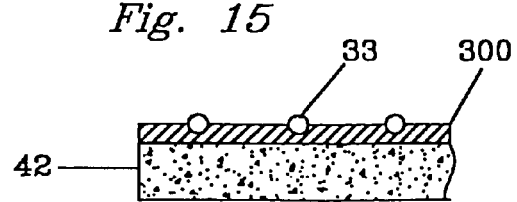
FIG. 15 illustrates a board containing pellets being applied to a concrete foundation.

Pellets are easily applied to a wide variety of uses. FIG. 12 illustrates pellets sprayed 50 onto a concrete structure surface 40. FIG. 15 illustrates treating a surface by placing pellets 33 on preformed boards 300.

Figure 13:
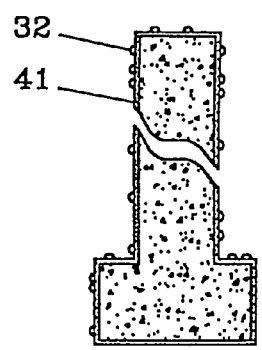
FIG. 13 illustrates a cross-sectional view of a concrete foundation after foam has been applied.

Pellets 32 are applied onto a surface 40 such as soil or concrete via a foam 41 as illustrated in FIG. 13. The pellets are first incorporated into a foam in a manner known in the art. The foam 41 containing the fine pellets is then sprayed 50 as illustrated onto the surface 41 via a motorized sprayer 70 in FIG. 12 so as to provide a protective coating for the surface. The pellets 32 then release the insecticide to create a protective barrier in the soil to protect the wood from harmful insects. For best results, the foam 50 is comprised of polyurethane. It is also possible to use silicone, polyester, or polyvinyl acetate. The pellets 32 can vary in size depending upon the foam thickness and the desired concentration of insecticide in the exclusion zone. The thickness of the foam to be applied to a surface can vary according to user's preference. The exclusion zone can be maintained for at least 6 years. In addition to being used as a carrier for insecticide, the foam also cures cement and acts as an insulator.

Figure 14:
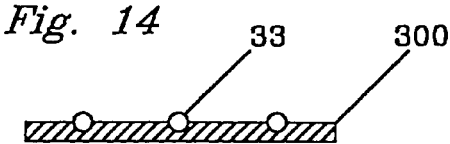
FIG. 14 illustrates pellets set on a board.

A preformed board with embedded pellets 33 can also be utilized as an embodiment of this invention as illustrated in FIG. 14. This board 300 can be made of any type of material which can suitably hold the pellets 33. Preferably, the board is comprised of styrofoam which is registered as a Dow trademark. The board can be applied in any variety of fashions and can also work as an insulating device. One manner of application is illustrated in FIG. 15, where the board 300 with pellets 33 is placed above a concrete surface 42. The embedded pellets are regularly spaced with the spacing being specified by the devised amount of insecticide.

Figure 16:
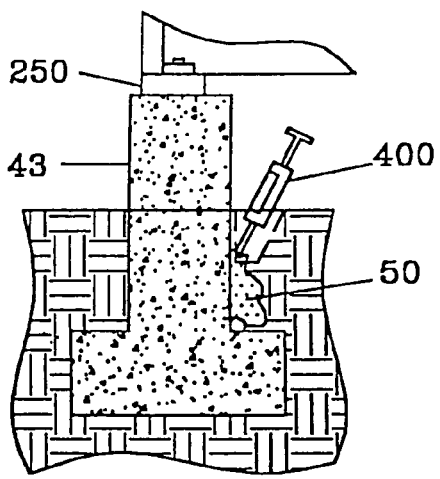
FIG. 16 illustrates a hot-melt injection.
Figure 17:
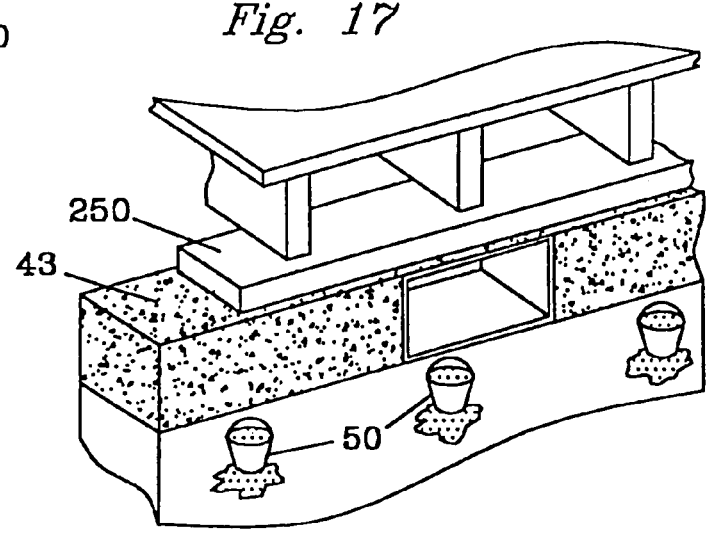
FIG. 17 illustrates the spacing of the hot-melt injunction.

In another embodiment as shown in FIGS. 16 and 17, the controlled release device comprising the polymer matrix and insecticide can be applied via a hot melt. This embodiment is designed to meet the needs of structures already in place. As stated above, the polymer matrix can comprise any of the four above-named polymer groups. Similarly, any of the above-named insecticides can be utilized. However, it is preferable to use high or low density polyethylene with either a pyrethrin. Although tailored to the user, the concentrations of the various substances in the hot-melt application should range from about 70 to about 95 for the polymer, from about 5 to about 30 for the insecticide and from about 0 to about 30 for filler/carrier for optimal results.

FIG. 16 shows hot melt 50 being injected by a syringe 400 into the ground near a concrete foundation 43. The concrete structure 43 supports a wooden structure 250. FIG. 17 shows the spacing between the hot melt 50 which has already been injected into the ground.

Figure 18:
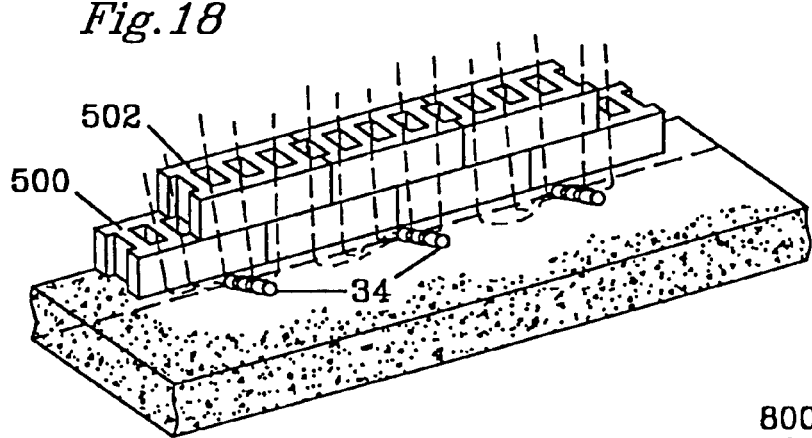
FIG. 18 illustrates a plug fumigating cement blocks.
Figure 19:
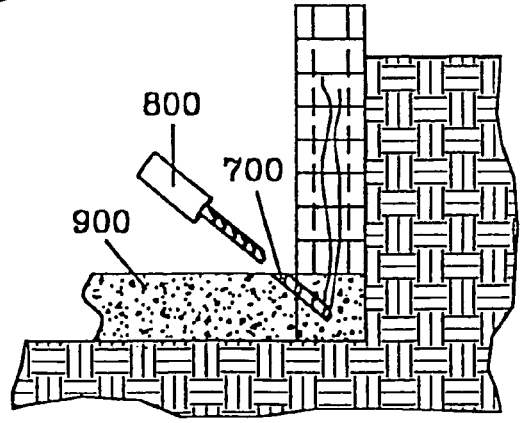
FIG. 19 illustrates a mode of applying plugs to fumigate cement blocks.

In another embodiment, FIGS. 18 and 19 illustrate the use of insecticide to fumigate a structure 500. By injecting or placing the controlled release device in or near a structure which can be fumigated, the insecticide release from the controlled release device can vaporize thereby fumigating the structure. FIG. 18 illustrates the use of plugs 34 to fumigate a structure 500 made of building blocks 502. Similarly, FIG. 19 illustrates a mode of applying the controlled release device by using a drill 800 to bore a hole 700 into a cement slab 900. Once inserted, the plug is able to fumigate the structure.

CURRENTLY PREFERRED EMBODIMENT

Figure 20:
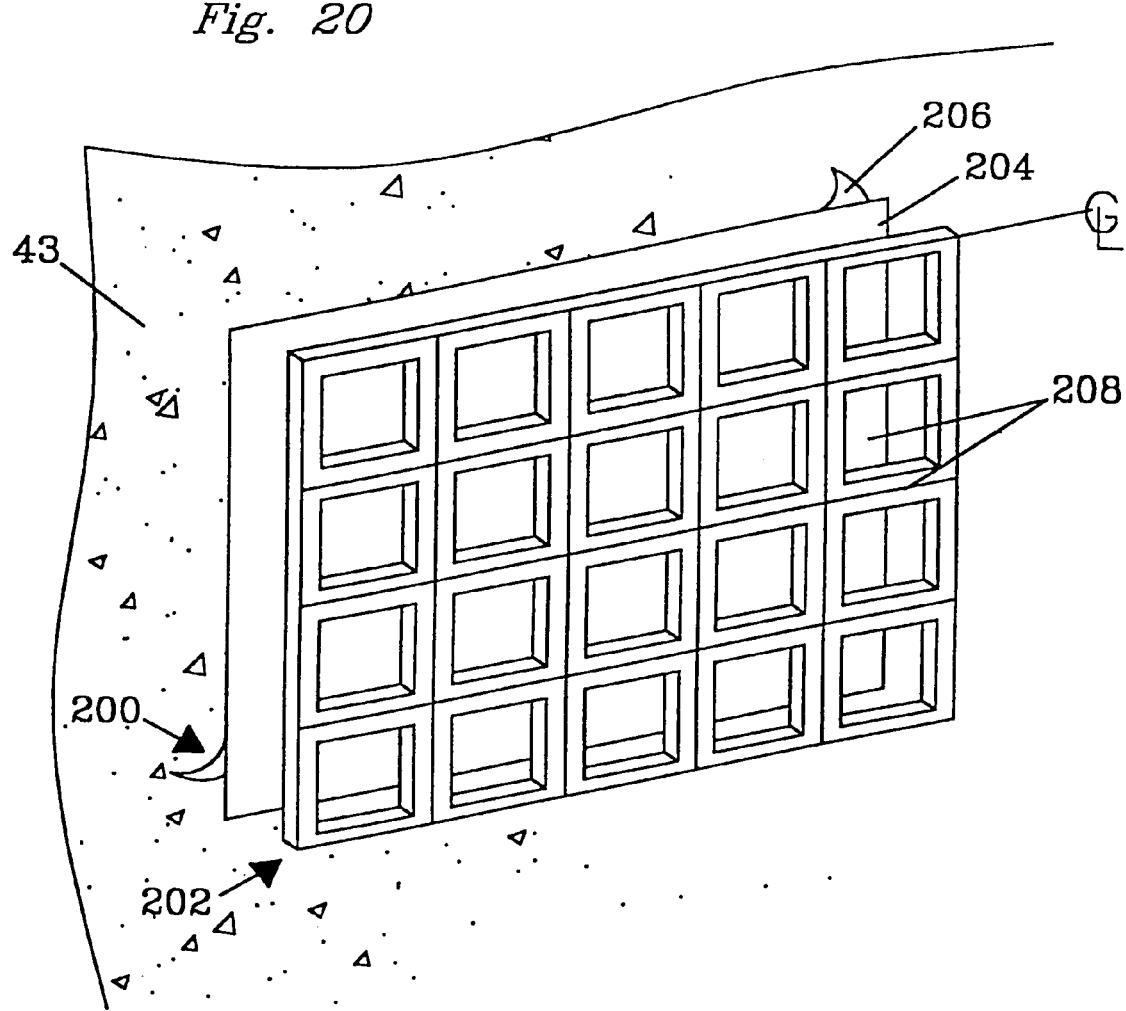
FIG. 20 shows a layered apparatus of the present invention.

The currently preferred embodiment of the apparatus of the present invention as shown in FIG. 20 combines a first polymer 200 of medium or high density polymer having a low vapor pressure insecticide with a second polymer 202 of low density having a more volatile, vis higher vapor pressure, insecticide. High, medium and low density are terms well known in the polymer art referring to the degree of cross linking within a polymer. High vapor pressure is defined as vapor pressure in excess of about 1 millipascal and preferably ranges from about 10 millipascals to about 100 millipascals. Low vapor pressure is defined as less than 1 millipascal and preferably ranges from about 0.05 millipascals to about 0.5 millipascals. The first polymer 200 preferably has a thickness in the range from about 1/32 to 1/8 inch. The low vapor pressure insecticide, is preferably permethrin or lambdacyhalothrin. The preferred material of the first polymer 200 is selected from among polyurethane, high density polyethylene and polypropylene. The second polymer 202 is placed adjacent to and, preferably attached to the first polymer 200. It is preferred that the first polymer 200 be water and radon impermeable. Hence, the first polymer 200 is preferably a sheet that may be a film or spun bonded. According to the present invention, the first polymer 200 may be in two sub-parts with one sub-part 204 a permeable medium or high density polymer containing the low vapor pressure insecticide and another sub-part 206 an impermeable layer having no insecticide within. The impermeable layer has an advantage for handling of preventing or reducing exposure/contact of the installer with the bioactive chemical. The impermeable layer may be, for example Mylar, saran or saranax.

The second polymer 202 is a low density polymer, preferably an ethylene vinyl acetate, a low density polyethylene or blend thereof. The more volatile or higher vapor pressure insecticide placed within the second polymer is preferably a synthetic pyrethroid, for example tefluthrin.

The second polymer 202 may be in the form of pellets as previously described and the first and second polymers deployed with the first polymer under a sill plate on a foundation and the second polymer scattered in the soil adjacent the foundation. More preferably, the second polymer 202 is in the form of an open mesh, either woven or non-woven as shown. Mesh openings may range from touching but not sealed to about 1 to four inches square and ribs 208 having a cross section width of from about 1 mil to about 1/8 inch. A scrim that can be made from polyethylene, polypropylene, or polyester may be used as the mesh. With a first polymer 200 sheet and a second polymer 202 open mesh, the apparatus of the combination of the first and second polymers 200, 202 is preferably placed below grade. The first polymer sheet 200 is placed adjacent the second polymer 202 open mesh with the first polymer 200 sheet in contact or near a foundation 43 and between the foundation and the second polymer 202 open mesh. The mesh material may absorb bioactive chemical and contribute to the reservoir of bioactive material.

In operation, the first polymer 200 maintains a physical/chemical barrier against insect intrusion. However, because of the slow release of the first polymer 200, very little insecticide is released that would be available to create an exclusion zone within about the first year after installation. In addition, it is impossible to install a defect free barrier because of penetrations, for example electrical and plumbing, and because of punctures or tears during construction. Accordingly, the second polymer 202 is deployed to create exclusion zones within a few days of installation thereby preventing insect access through the imperfections of the first polymer 200. The first polymer 200, therefore has three functions: insect barrier, vapor/moisture barrier, and radon barrier. The first polymer 200 is designed to last at least 10 years and preferably up to and in excess of 20 years. The second polymer 202 is designed to last at least 5 years and preferably up to about 10 years. By the time that the second polymer 202 is depleted and no longer effective against insects, the first polymer 200 will have developed a concentration of released insecticide sufficient to maintain the exclusion zone.

The following examples are provided by way of explanation. As such, these examples are not viewed as limiting the scope of the invention as defined by the appended claims.

Example 1

Experiments were conducted to determine the release rate of chlorpyrifos. Loading rates for the insecticide were either 5 wt % or 10 wt %, depending on polymer. Release rates were determined for all devices at 50° C.

Polymers evaluated included low melt polyethylene, polyurethane, two epoxies, silicone rubber, and a low melt polyethylene high in waxes to reduce thermal decomposition of the chlorpyrifos. Studies indicated that excessive thermal decomposition of the chlorpyrifos-occurred at temperatures in excess of approximately 240° C.; thus, polymer selection was restricted to formulations not requiring excessive heat processing.

Table 1 provides a summary of the results from these studies. Overall, polymer compatibility with chlorpyrifos did not appear to present a problem with the loading rates employed. There was some loss of physical integrity of the polyurethane polymer employed, however, the other polymer systems exhibited no visible degradation at 50° C. Release rates ranged from 10 µg/cm$^2$/da for the silicone rubber, to 0.3 µg/cm$^2$/da for Epoxy B.

Using the data provided in Table 1, an estimated product longevity can be approximated. Assuming a device wt. of 0.5 g, with 10% load, then 50 mg of chlorpyrifos is available for release. Thus, for a polymer system having an area of 4 cm$^2$, and a release rate of 1 µg/cm$^2$/da, there is sufficient insecticide to last 30 years at elevated temperature. These calculations indicate that a variety of insecticidal products are possible.

TABLE 1

Polymer Formulations and Release Rates for Candidate Systems Employing Chlorpyrifos.

| Polymer Class | Chlorpyrifos Content (%) | Release Rate (µg/cm$^2$/da)[a] |
|---|---|---|
| Polyurethane | 5 | 2.1 ± 1.4[b] |
| Epoxy A | 5 | <0.1 |
| Silicone | 5 | 10.3 ± 3.5 |
| Urethane | 10 | 1.0 ± 0.3 |
| Epoxy B | 10 | 0.3 ± 0.1 |
| PE + Wax | 10 | 1.9 ± 0.3 |

[a]Release rates performed at 50° C.
[b]Material exhibited excessive cracking at elevated temperature Example 2

Studies were also conducted with similar polymer systems as in Example 1 but with 80% pure pyrethrin. Release rates at 40° C. are provided in Table 2.

TABLE 2

Polymer Formulations and Release Rates for Candidate Systems Employing Pyrethrin I.

| Polymer Class | Pyrethrin I Content (%) | Release Rate (µg/cm$^2$/da)[a] |
|---|---|---|
| Epoxy A | 10 | 0.5 ± 0.2 |
| Silicone | 10 | 21.2 ± 5.4 |
| Urethane | 10 | 15.7 ± 7.1 |
| Epoxy B | 10 | 0.2 ± 0.1 |

[a]Release rates performed at 40° C.

The release rates were highest for urethane and silicone and lowest for the epoxies. Substantial variability in release rates were encountered and appropriate binders will need to be evaluated.

From the data in Table 2, simple calculations can be performed to determine the possible life of the insecticide systems. As stated in Example 1, there are many variables which can alter the lifetime of an exclusion zone.

Example 3

Controlled release devices were made and tested to obtain their release rates. All thermoplastic polymers were formulated with 10 percent pesticide, 3 or 7 percent carbon black to absorb liquid pesticide and 83 to 87 percent by weight of polymer and injection molded into thin sheets about ⅛ inch thick. Specifically, devices made from thermoplastic polymers and deltamethrin and lambdacyhalothrin contained 3 percent of carbon black. The devices made from the remaining pesticides and thermoplastic polymers contained 7 percent of carbon black.

The devices made from S-113 urethane (a thermoset polymer) were made from a polymer mix containing 60% S-113, 40% castor oil and 5% of TIPA catalyst by weight. The polymer mix comprised 90% of the total weight of the device. The pesticide, deltamethrin, comprised the remaining 10% of the device. No carbon black was used in this device. The polymer/pesticide mixture was cast into a ⅛ inch thick sheet and heated at about 60° C. for about 40 to 60 minutes to cure the cast sheet.

One inch squares were then cut from the thin sheets that were injection molded or cast and the squares were tested for release rates. The following release rates were obtained:

| Pesticide | Polymer | Release Rate |
|---|---|---|
| Deltamethrin | S-113 urethane | 25.2 µg/cm$^2$/day |
| | Aromatic 80A | 16.8 µg/cm$^2$/day |
| | Pellethane 2102-80A | 8.8 µg/cm$^2$/day |
| | Pellethane 2102-55D | 8.0 µg/cm$^2$/day |
| | Alipmtic PS-49-100 | 7.2 µg/cm$^2$/day |
| Cypermethrin | polyurethane 3100 | 0.4 µg/cm$^2$/day |
| | polyurethane 2200 | 0.7 µg/cm$^2$/day |
| | EVA 763 | 27.3 µg/cm$^2$/day |
| | Polyethylene MA 778-000 | 4.6 µg/cm$^2$/day |
| Lambdacyhalothrin | polyurethane 3100 | 0.4 µg/cm$^2$/day |
| | polyurethane 2200 | 0.7 µg/cm$^2$/day |
| | EVA 763 | 27.3 µg/cm$^2$/day |
| | Polyethylene MA 778-000 | 4.6 µg/cm$^2$/day |
| Tefluthrin | polyurethane 3100 | 6.4 µg/cm$^2$/day |
| | Polyurethane 2200 | 25.0 µg/cm$^2$/day |
| | EVA 763 | 40.4 µg/cm$^2$/day |
| | Polyethylene MA 778-000 | 27.0 µg/cm$^2$/day |
| Permethrin | polyurethane 3100 | 1.4 µg/cm$^2$/day |
| | Polyurethane 2200 | 1.3 µg/cm$^2$/day |
| | EVA 763 | 28.5 µg/cm$^2$/day |
| | Polyethylene MA 778-000 | 4.0 µg/cm$^2$/day |

Example 4

An experiment was conducted to determine the effect of lambdacyhalothrin (pyrethroid) concentration and insecticide/polymer combination on release rate of insecticide from the polymer. The data are summarized in Table 4.

TABLE 4

Release Rate for Polymer/Pyrethroid Concentration Combinations.

| Polymer | Pyrethroid Conc. (wt %) | Release Rate (mg/cm$^2$/day) |
|---|---|---|
| Ethylvinyl Acetate (EVA) | 1 | 0.3 |
| | 5 | 2.2 |
| | 10 | 2.5 |
| Polyurethane | 1 | 0.9 |
| | 5 | 4.4 |
| | 10 | 8.3 |
| Polyurethane/EVA (50/50) | 1 | 2.6 |
| | 5 | 7.2 |
| | 10 | 9.1 |

Example 5

An experiment was conducted to determine the effectiveness of the exclusion zone against termites. Two species of termites were selected for the tests: Eastern subterranean termite because it is the most common, and Formosan subterranean termite because it is the most aggressive.

Test cells were assembled with glass containers. Wood shavings were placed in the bottom of the containers. Insecticide impregnated polymer was placed over the wood chips in a manner that no path or opening existed from above the impregnated polymer to the wood chips. A nutrient free auger was placed above the impregnated polymer. The surface of the auger was the zero datum and the impregnated polymer was mounted at a distance of 5 cm below the surface of the auger. Termites were placed on the surface of the auger and their progress through the auger toward the impregnated polymer noted each day.

The impregnated polymer combinations are shown in Table 5a.

TABLE 5a

Release Rate for 10 wt % Pyrethroid

| Polymer | Pyrethroid | Release Rate ($mg/cm^2/day$) |
|---|---|---|
| Ethylvinyl acetate | Permethrin | 3.9 |
| Ethylvinyl acetate | Tefluthrin | 4.3 |
| Ethylvinyl acetate | Tefluthrin (2 wt % fatty acid) | 3.2 |
| Polyethylene | Permethrin | 1.4 |
| Polyethylene | Tefluthrin | 2.2 |
| Polyethylene | Tefluthrin (2 wt % fatty acid) | 2.0 |

Figure 21:
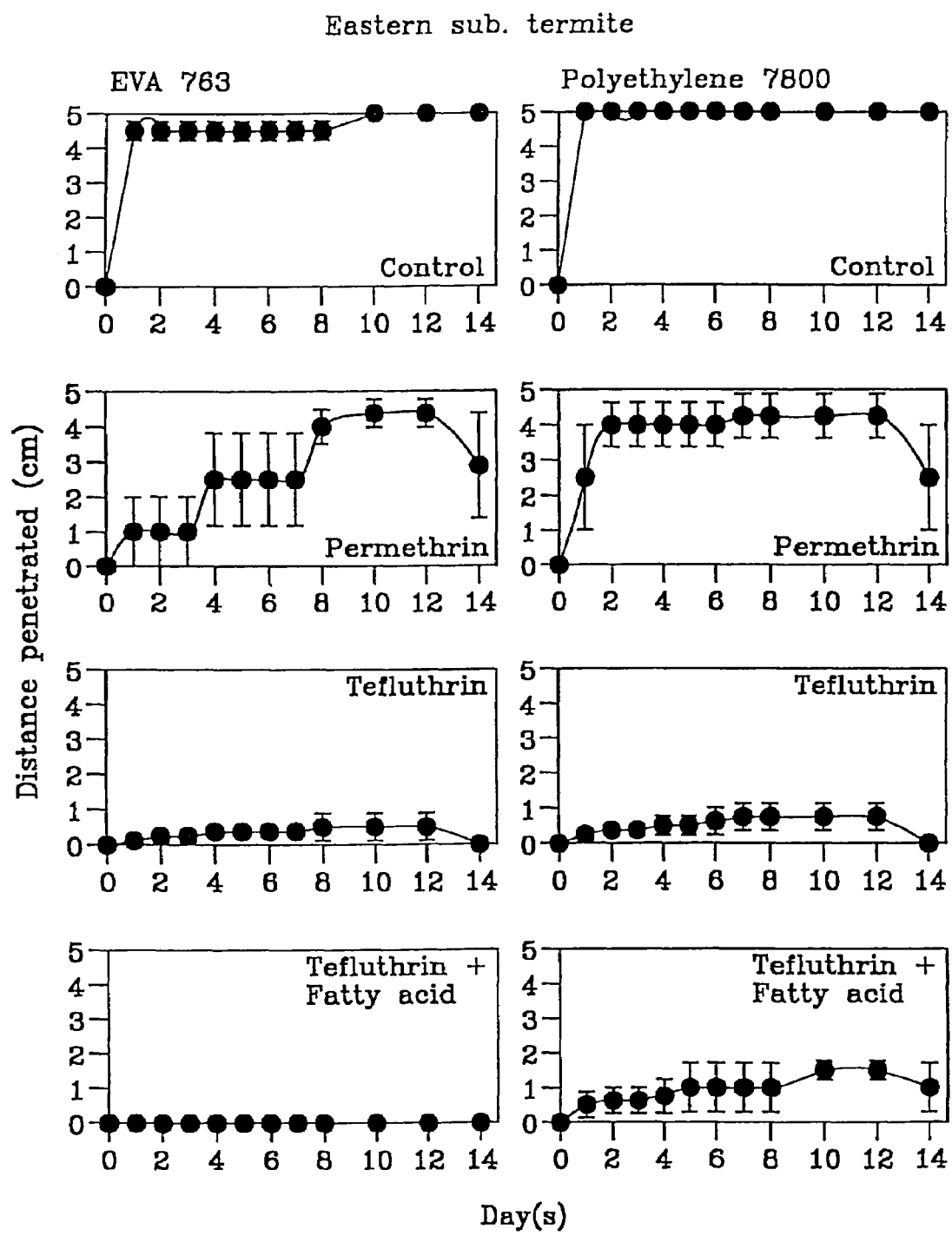
FIG. 21 shows repellency of Eastern subterranean termites.
Figure 22:
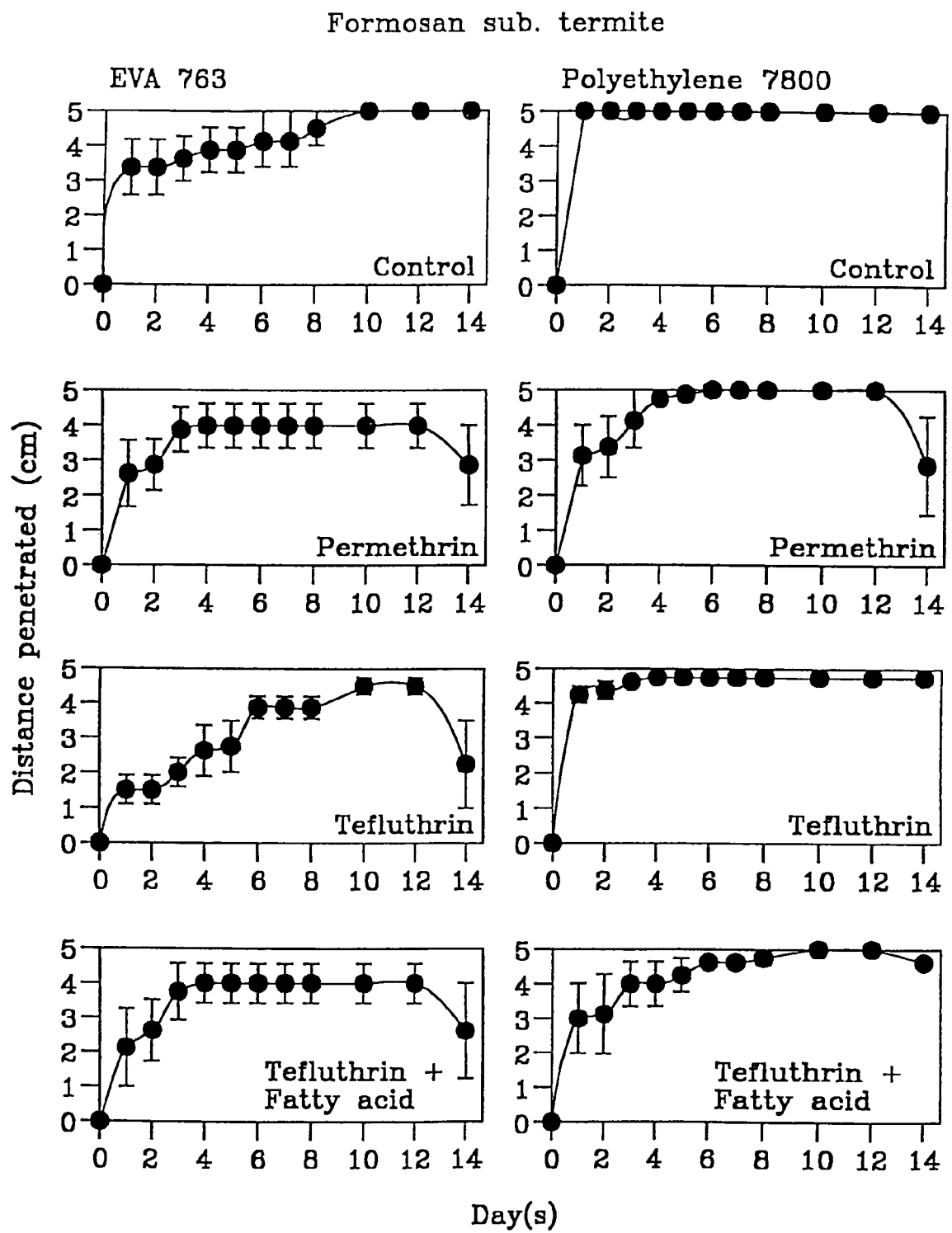
FIG. 22 shows repellency of Formosan subterranean termites.

Controls having no pyrethroid in a polymer barrier were also used. Results are shown in FIG. 21 and FIG. 22. In all controls, the termites ate through the polymer and obtained access to the wood chips. The rate of access through ethylvinyl acetate was slower than for polyethylene. For all impregnated polymers, there was no penetration. Because the Formosan subterranean termites are so aggressive, they came closer to the impregnated polymer than the less aggressive Eastern subterranean termites. In fact, the polyethylene with permethrin suffered mandible marks from the Formosan termites, but no holes or penetration. After about 12-14 days, even the Formosan termites were discouraged by the release of insecticide and retreated from impregnated polymer.

Example 6

An experiment was conducted to demonstrate the effect of a binding carrier on release rate. The active chemicals were tefluthrin and lambdacyhalothrin in an amount of 5 wt %, the binding carrier was carbon black in amounts of 0 wt % and 10 wt %, with the balance high density polyethylene (MA 778-000). Release rates were measured at 6 weeks after fabrication wherein samples were wiped weekly to remove surface accumulation of released active chemical.

Results are shown in Table 6.

TABLE 6

Release Rates for 0 wt % and 10 wt % Carbon Black

| Active Chemical | Carbon Black (wt %) | Release Rate ($\mu g/cm^2/day$) |
|---|---|---|
| tefluthrin | 0 | 3.13 |
| tefluthrin | 10 | 0.71 |
| lambdacyhalothrin | 0 | 1.78 |
| lambdacyhalothrin | 10 | 0.81 |
| lambdacyhalothrin | 20 | 0.61 |

CLOSURE

From the foregoing description one skilled in the art can easily ascertain the essential characteristics of this invention and without department from the spirit and scope of the invention thereof can make changes and modifications of the invention in order to adapt it to the various usages and conditions. It is intended that the scope of the invention be defined by the following claims including all equivalents which are intended to define this invention.

We claim:

1. A method of making a multi-layer barrier for preventing wood pests from accessing a wooden structure for a prolonged period of time and with a minimal impact on the environment, the method comprising:

forming a first layer comprising a first polymer, a pesticide in liquid, and a carrier by binding the pesticide to the carrier to form a pesticide-carrier mixture, the pesticide selected from isofenphos, fenvalerate, cypermethrin, permethrin, tefluthrin, lambdacyhalothrin, cyfluthrin, deltamethrin, and combinations thereof and the carrier is selected from carbon black, activated carbon, alumina, silicoaluminate, hydroxyapatite and combinations thereof, mixing the first polymer and the pesticide-carrier mixture to form a mixture, the first polymer is selected from high density polyethylene, low density polyethylene, ethylene vinyl acetate, vinyl acetate, urethane, polyester, a thermoplastic elastomer, silicone, neoprene, polyethylene, polyurethane, polypropylene, polybutylene, epoxy polymers, polyamides, acrylate-styrene-acrylonitrile, aromatic polyesters, unsaturated polyesters, polyisoprene, and combinations thereof, melting the mixture, and solidifying the mixture to form a polymer matrix, the pesticide-carrier mixture bound within the polymer matrix of the first layer, the first layer being permeable to the pesticide; and combining the first layer with a second layer, the second layer comprising a second polymer, the second layer being substantially non-releasing and impermeable in that the pesticide is released from the barrier at a rate of less than 0.4 $\mu g/cm^2/day$, the release rate being sufficient to prevent wood pests from breaching the barrier.

2. The method of claim 1, wherein the pesticide comprises lambdacyhalothrin.

3. The method of claim 1, wherein the concentration of the pesticide is at least 1 wt % of the polymer matrix.

4. The method of claim 1, wherein the concentration of the pesticide is at least 5 wt % of the polymer matrix.

5. The method of claim 1, wherein the first polymer comprises low density polyethylene.

6. The method of claim 1, wherein the carrier comprises carbon black.

7. The method of claim 1, wherein the polymer matrix continues releasing the pesticide for at least six years.

8. The method of claim 1, wherein the pesticide is released from the barrier at a rate which is less than 0.1 µg/cm²/day.

9. The method of claim 1, wherein the pesticide is released from the barrier at a rate which is less than 0.05 µg/cm²/day.

10. The method of claim 1, further comprising the first layer is in the form of a sheet, strip or pellet.

11. The method of claim 1, wherein the second layer is a sheet made from polyethylene terephthalate film, a copolymer of vinylidene chloride and vinyl chloride, or a coextruded multi-layered barrier film.

12. The method of claim 1, further comprising the step of forming at least one additional layer located adjacent the first layer and comprising a third polymer and a second pesticide, wherein the third polymer forms a second polymer matrix and the second pesticide is bound within the second polymer matrix.

13. The method of claim 12, wherein the at least one said additional layer is in the form of a mesh.

14. The method of claim 1, further comprising the step of forming a third layer located on the opposite side of the first layer, the third layer being made of a strength and puncture resistant material.

15. The method of claim 14, wherein the strength and puncture resistant material is a polymeric scrim.

16. The method of claim 1, further comprising the step of binding the pesticide to the carrier to form a bound friable mix.

17. The method of claim 1, wherein the barrier further comprises a metallized layer.

18. A method of making a multi-layer barrier for preventing wood pests from accessing a wooden structure for a prolonged period of time and with a minimal impact on the environment, the method comprising:
    forming a first layer comprising a first polymer, a pesticide in liquid, and a carrier by binding the pesticide to the carrier to form a pesticide-carrier mixture, and mixing the first polymer and the pesticide-carrier mixture to form a mixture, the carrier being selected from carbon black, activated carbon, alumina, silicoaluminate, hydroxyapatite, and combinations thereof;
    melting the mixture, and solidifying the mixture to form a polymer matrix, the pesticide carrier mixture bound within the polymer matrix of the first layer, the first layer being permeable to the pesticide; and
    combining the first layer with a second layer, the second layer comprising a second polymer, the second layer being substantially non-releasing and impermeable in that the pesticide is released from the barrier at a rate of less than 0.4 µg/cm²/day, the release rate being sufficient to prevent wood pests from breaching the barrier.

19. The method of claim 18, wherein the pesticide is selected from isofenphos, fenvalerate, cypermethrin, permethrin, tefluthrin, lambdacyhalothrin, cyfluthrin, deltamethrin, and combinations thereof.

20. The method of claim 18, wherein the pesticide comprises lambdacyhalothrin.

21. The method of claim 18, wherein the concentration of the pesticide is at least 1 wt % of the polymer matrix.

22. The method of claim 18, wherein the concentration of the pesticide is at least 5 wt % of the polymer matrix.

23. The method of claim 18, wherein the first polymer is selected from high density polyethylene, low density polyethylene, ethylene vinyl acetate, vinyl acetate, urethane, polyester, a thermoplastic elastomer, silicone, neoprene, polyethylene, polyurethane, polypropylene, polybutylene, epoxy polymers, polyamides, acrylate-styrene-acrylonitrile, aromatic polyesters, unsaturated polyesters, polyisoprene, and combinations thereof.

24. The method of claim 18, wherein the first polymer comprises low density polyethylene.

25. The method of claim 18, wherein the carrier comprises carbon black.

26. The method of claim 18, wherein the polymer matrix continues releasing the pesticide for at least six years.

27. The method of claim 18, wherein the pesticide is released from the barrier at a rate which is less than 0.1 µg/cm²/day.

28. The method of claim 18, wherein the pesticide is released from the barrier at a rate which is less than 0.05 µg/cm²/day.

29. The method of claim 18, further comprising the first layer is in the form of a sheet, strip or pellet.

30. The method of claim 18, wherein the second layer is a sheet made from polyethylene terephthalate film, a copolymer of vinylidene chloride and vinyl chloride, or a coextruded multi-layered barrier film.

31. The method of claim 18, further comprising the step of forming at least one additional layer located adjacent the first layer and comprising a third polymer and a second pesticide, wherein the third polymer forms a second polymer matrix and the second pesticide is bound within the second polymer matrix.

32. The method of claim 31, wherein the at least one said additional layer is in the form of a mesh.

33. The method of claim 18, further comprising the step of forming a third layer located on the opposite side of the first layer, the third layer being made of a strength and puncture resistant material.

34. The method of claim 33, wherein the strength and puncture resistant material is a polymeric scrim.

35. The method of claim 18, wherein the barrier further comprises a metallized layer.

36. A method for creating an exclusion zone of pesticide for protecting a wooden structure against contact by wood pests comprising:
    placing a multi-layer barrier at entry points to the structure, the barrier having an outside surface and comprising a polymeric matrix and a pesticidally effective amount of pesticide for wood pests within the matrix, the matrix having an outside surface, the multi-layer barrier comprising:
    a first layer comprising a first polymer, a pesticide, and a carrier, wherein the first polymer forms a polymer matrix, the pesticide bound to the carrier to form a pesticide-carrier mixture, the polymer matrix being formed by mixing the first polymer and the pesticide-carrier mixture to form a mixture, melting the mixture, and solidifying the mixture to form the polymer matrix, the pesticide-carrier mixture bound within the polymer matrix; and
    a second layer located adjacent the first layer, the second layer comprising a second polymer, the second layer being substantially non-releasing and impermeable in that the pesticide is released from the barrier at a rate of less than 0.4 µg/cm²/day; and
    allowing the pesticide to release onto the outside surface of the matrix and accumulate on the outside surface of the matrix to form an exclusion zone, the exclusion zone being effective in protecting the wooden structure against contact by wood pests for a prolonged period of time and with a minimal impact on the environment.

37. The method of claim 36, wherein the pesticide is selected from isofenphos, fenvalerate, cypermethrin, permethrin, tefluthrin, lambdacyhalothrin, cyfluthrin, deltamethrin, and combinations thereof.

38. The method of claim 36, wherein the first polymer is selected from high density polyethylene, low density polyethylene, ethylene vinyl acetate, vinyl acetate, urethane, polyester, a thermoplastic elastomer, silicone, neoprene, polyethylene, polyurethane, polypropylene, polybutylene, epoxy polymers, polyamides, acrylate-styrene-acrylonitrile, aromatic polyesters, unsaturated polyesters, polyisoprene, and combinations thereof.

39. The method of claim 36, wherein the carrier is selected from carbon black, activated carbon, alumina, silicoaluminate, hydroxyapatite and combinations thereof.

40. A method for creating an exclusion zone of pesticide for protecting a wooden structure against contact by wood pests comprising:

placing a multi-layer barrier at entry points to the structure, the barrier having an outside surface and comprising a polymeric matrix and a pesticidally effective amount of pesticide for wood pests within the matrix, the matrix having an outside surface, the multi-layer barrier comprising:

a first layer comprising a first polymer and a pesticide, wherein the first polymer forms a polymer matrix, the polymer matrix being formed by mixing the pesticide with the first polymer to form a mixture, melting the mixture, and solidifying the mixture to form the polymer matrix, the pesticide bound within the polymer matrix; and a second layer located adjacent the first layer, the second layer comprising a second polymer, the second layer being substantially non-releasing and impermeable in that the pesticide is released from the barrier at a rate of less than 0.4 $\mu g/cm^2/day$; and allowing the pesticide to release onto the outside surface of the matrix and accumulate on the outside surface of the matrix to form an exclusion zone, the exclusion zone being effective in protecting the wooden structure against contact by wood pests for a prolonged period of time and with a minimal impact on the environment.

41. The method of claim 40, wherein the pesticide is selected from isofenphos, fenvalerate, cypermethrin, permethrin, tefluthrin, lambdacyhalothrin, cyfluthrin, deltamethrin, and combinations thereof.

42. The method of claim 40, wherein the pesticide comprises lambdacyhalothrin.

43. The method of claim 40, wherein the concentration of the pesticide is at least 1 wt % of the polymer matrix.

44. The method of claim 40, wherein the concentration of the pesticide is at least 5 wt % of the polymer matrix.

45. The method of claim 40, wherein the first polymer is selected from high density polyethylene, low density polyethylene, ethylene vinyl acetate, vinyl acetate, urethane, polyester, a thermoplastic elastomer, silicone, neoprene, polyethylene, polyurethane, polypropylene, polybutylene, epoxy polymers, polyamides, acrylate-styrene-acrylonitrile, aromatic polyesters, unsaturated polyesters, polyisoprene, and combinations thereof.

46. The method of claim 40, wherein the first polymer comprises low density polyethylene.

47. The method of claim 40, wherein the polymer matrix continues releasing the pesticide for at least six years.

48. The method of claim 40, wherein the pesticide is released from the barrier at a rate which is less than 0.1 $\mu g/cm^2/day$.

49. The method of claim 40, wherein the pesticide is released from the barrier at a rate which is less than 0.05 $\mu g/cm^2/day$.

50. The method of claim 40, further comprising the first layer is in the form of a sheet, strip or pellet.

51. The method of claim 40, wherein the second layer is a sheet made from polyethylene terephthalate film, a copolymer of vinylidene chloride and vinyl chloride, or a coextruded multi-layered barrier film.

52. The method of claim 40, further comprising the step of forming at least one additional layer located adjacent the first layer and comprising a third polymer and a second pesticide, wherein the third polymer forms a second polymer matrix and the second pesticide is bound within the second polymer matrix.

53. The method of claim 52, wherein the at least one said additional layer is in the form of a mesh.

54. The method of claim 40, further comprising the step of forming a third layer located on the opposite side of the first layer, the third layer being made of a strength and puncture resistant material.

55. The method of claim 54, wherein the strength and puncture resistant material is a polymeric scrim.

56. The method of claim 40, wherein the barrier further comprises a metallized layer.

* * * * *